(12) United States Patent
Furstenberg et al.

(10) Patent No.: US 10,416,049 B2
(45) Date of Patent: Sep. 17, 2019

(54) PROCESSING OF SOLID MICRON SIZED PARTICLES FOR RAPID DEPOSITION ON SUBSTRATE SURFACES WITH UNIFORM PARTICLE DISTRIBUTION

(71) Applicant: The Government of the United States of America, as represented by the Secretary of the Navy, Arlington, VA (US)

(72) Inventors: Robert Furstenberg, Burke, VA (US); Thomas Fischer, Grossneuhausen (DE); Viet K. Nguyen, Gaithersburg, MD (US); R Andrew McGill, Lorton, VA (US); Chris Kendziora, Burke, VA (US); Michael Papantonakis, Washington, DC (US)

(73) Assignee: The Government of the United States of America, as represented by the Secretary of the Navy, Washington, DC (US)

( * ) Notice: Subject to any disclaimer, the term of this patent is extended or adjusted under 35 U.S.C. 154(b) by 145 days.

(21) Appl. No.: 15/479,461

(22) Filed: Apr. 5, 2017

(65) Prior Publication Data
US 2017/0284928 A1 Oct. 5, 2017

Related U.S. Application Data

(60) Provisional application No. 62/318,651, filed on Apr. 5, 2016.

(51) Int. Cl.
*G01N 1/28* (2006.01)
*G01N 15/10* (2006.01)
(Continued)

(52) U.S. Cl.
CPC .............. *G01N 1/28* (2013.01); *B07B 1/52* (2013.01); *B07B 13/16* (2013.01); *G01N 15/10* (2013.01);
(Continued)

(58) Field of Classification Search
CPC ... G01N 2015/0019; G01N 15/00–2015/1497; G01N 51/10;
(Continued)

(56) References Cited

U.S. PATENT DOCUMENTS 5,530,533 A 6/1996 Wallace
5,656,138 A 8/1997 Scobey et al.
(Continued)

FOREIGN PATENT DOCUMENTS

JP 2008-100132 A 5/2008
WO 2003/053791 A2 7/2003

OTHER PUBLICATIONS

International Search Report and Written Opinion issued in counterpart application PCT/US2017/026052.

*Primary Examiner* — Michael P LaPage
(74) *Attorney, Agent, or Firm* — US Naval Research Laboratory; Rebecca L. Forman

(57) ABSTRACT

This application relates generally to a method and apparatus to deposit particles onto one or more coupons, and harvest particles from one or more coupons, which may beneficially provide a more uniform or localized distribution of particles over a specified area on each coupon. The application relates to a method and apparatus for depositing particles onto one or more coupons using a sieve. The application also relates to a method and apparatus for depositing particles onto one or more coupons using a dust storm. The particle loadings achieved on each coupon or across an individual coupon may be substantially uniform. The to a laser-based method and apparatus for transferring particles deposited at localized points on a source coupon to a different substrate for further use.

5 Claims, 17 Drawing Sheets

(51) Int. Cl.
  *B07B 1/52* (2006.01)
  *B07B 13/16* (2006.01)
(52) U.S. Cl.
  CPC ............... *B07B 1/522* (2013.01); *B07B 1/524* (2013.01); *B07B 1/526* (2013.01); *B07B 1/528* (2013.01); *G01N 2001/2893* (2013.01); *G01N 2015/1018* (2013.01)
(58) Field of Classification Search
  CPC ... G01N 2015/1081; G01N 2015/1087; G01N 2015/1093; G01N 21/01; G01N 1/28; G01N 1/286; G01N 2001/2893; G01N 2015/1018; B07B 1/18; B07B 1/28; B07B 1/30; B07B 1/343; B07B 1/346; B07B 1/52; B07B 13/16; B07B 1/526; B07B 1/524; B07B 1/528; B07B 1/522; B02C 17/184

See application file for complete search history.

(56) References Cited

U.S. PATENT DOCUMENTS

| | | | |
|---|---|---|---|
| 6,023,981 A * | 2/2000 | Phillips | G01N 1/2205 73/863.23 |
| 6,101,886 A * | 8/2000 | Brenizer | B01D 45/08 55/308 |
| 8,973,759 B2 | 3/2015 | Ichikawa et al. | |
| 9,022,220 B2 | 5/2015 | Ozeki et al. | |
| 2007/0107495 A1* | 5/2007 | Kim | G01N 15/0272 73/31.02 |
| 2007/0277626 A1* | 12/2007 | Saitoh | B01D 46/0002 73/863.23 |
| 2014/0197077 A1* | 7/2014 | Rothman | B03B 1/04 209/163 |
| 2014/0291214 A1 | 10/2014 | Vasquez et al. | |
| 2015/0021238 A1* | 1/2015 | Gandhi | B07B 1/06 209/235 |
| 2016/0184866 A1* | 6/2016 | Iwamatsu | B07B 1/12 241/15 |

* cited by examiner

PROCESSING OF SOLID MICRON SIZED PARTICLES FOR RAPID DEPOSITION ON SUBSTRATE SURFACES WITH UNIFORM PARTICLE DISTRIBUTION

CROSS-REFERENCE TO RELATED APPLICATIONS

This application claims the benefit of priority under 35 U.S.C. § 119(e) from U.S. Provisional Application No. 62/318,651, filed on Apr. 5, 2016, the contents of which are incorporated herein by reference in their entirety.

TECHNICAL FIELD

This application relates generally to a method and apparatus to deposit particles onto one or more coupons, and harvest particles from one or more coupons, which may beneficially provide a more uniform or localized distribution of particles over a specified area on each coupon. The application relates to a method and apparatus for depositing particles onto one or more coupons using a sieve. The application also relates to a method and apparatus for depositing particles onto one or more coupons using a dust storm. The particle loadings achieved on each coupon or across an individual coupon may be substantially uniform. The application further relates to a laser-based method and apparatus for transferring particles deposited at localized points on a source coupon to a different substrate for further use.

BACKGROUND OF THE INVENTION

Standoff threat detection provides the capability to detect trace amounts of explosive, chemical, biological, or other agents without physical contact, obviating the need to obtain consent or cooperation from targets. Operation of detection equipment may be carried out at a significant distance, or up close to an object of interest, for example, from 0.5 to 100 meters away, reducing the level of risk posed to security personnel.

Such techniques are possible because the process of manufacturing threats, such as explosives, typically results in trace residues including particles of the threat material being left on persons and objects associated with manufacturing process. IR-laser spectroscopy and other techniques may be used to detect trace amounts of chemicals, such as explosives, which typically exhibit strong absorbance patterns in the mid-IR region. In order to calibrate the equipment to accurately detect trace amounts of threat materials and establish limits of detection for various threats, reference materials and standards are needed. The reference materials and standards may also be used to develop new techniques and new equipment to more accurately detect threats. Standards having known areal density are also desired, and control over variables including particle size, shape, and areal distribution would be beneficial. Given the very small amounts and volatility of the materials involved, production of consistent standard materials is difficult.

Techniques that may be used to deposit particles for detection, calibration, or further testing include inkjetting, aerosol spraying, pipetting, and spin coating onto a substrate.

Inkjetting has been popularized because of its use in printing, and has been adapted to print other chemicals of interest as a solution which dries on contact with an intended surface. Inkjetting is largely limited in its control of particle deposition by the solvent selected and its interaction or wetting with a surface. As the solution dries, complex processes can occur which may result in a wide variety of results, including coffee ring features, dome structures, isolated arrays of sub-micron sized particles, polycrystalline structures, and more. None of these represent typical particles found in fingerprints because their sizes and groupings do not match what is produced in an actual fingerprint. In addition, because drops deposited by inkjetting are typically very small, they evaporate very quickly and may trap substantial amounts of solvent in the produced crystal. The shapes, distribution, and content of particles is important in standoff detection technologies because the optical spectroscopies employed are often affected by the range of particle sizes involved and their chemical content. Further, inkjetting is inherently a serial process.

Sieving stacks are routinely used in laboratories to fractionate particles with one or more sieves. A collection pan is provided at the base of the stack in order to collect the processed particles. The stack is typically held together using a rigid support structure, and the base of the stack is positioned on a vibratory plate to couple a vibratory action to the sieving stack. The vibration causes the particles to move within each sieve and through suitable sieve openings into the receiving collection pan. An impact hammer action can also be applied to the top of the stack, and is typically operated at 1 Hz to assist the sieving action and reduce mesh pore blockages. The sieving stacks are typically operated in ambient air, which limits their practical use to particles of about 20 microns and above.

Using the conventional sieving stacks, the sieving of particles to a loading of between 10-100 micrograms/$cm^2$ can take tens of minutes, which is time consuming if multiple sieving operations are needed. In addition, there is no means to compensate for non-uniform sieving through a sieve membrane. Non-uniform sieving can result because of pore opening blockages, vibration nodes that form in the sieving membrane causing particle pooling in a sieving pan, and any sieving membrane/pan slope that leads to particle pooling towards one side of a sieving or collection pan. Feedback control to stop particle deposition when a desired amount of particles have been deposited is also lacking. These limitations present significant drawbacks when applying sieving or other techniques to fabricate samples or coupons which require controlled particle amounts and controlled particle distributions.

U.S. Pat. No. 9,022,220 describes a sieving system that includes a filter, a blade stirring a powder accumulated on the filter, a driver driving the blade, and a notifier for notifying a user of predetermined information regarding the status of the filter, based on a load on the driver while driving the blade.

U.S. Pat. No. 8,973,759 describes a sieving device including a hollow cylindrical body, a filter disposed at a bottom portion of the hollow cylindrical body, and a blade configured to rotate in close proximity to the filter around a rotation axis thereof, crossing the filter to thereby stir powder supplied to the hollow cylindrical body.

Each of these techniques uses a blade to stir and mix a powder present in sieve, and monitors the sieve for blockages.

However, none of the existing deposition techniques are able to adequately address the problems associated with non-uniform particle deposition, particularly in the context of standoff detection applications.

SUMMARY OF THE INVENTION

In contrast to the existing techniques described in the prior art, in some aspects, the present invention beneficially accelerates the sieving process while providing greater control over particle deposition. In some aspects, a blade is provided that is in contact with a sieving membrane. In other aspects, the invention only loads the sieve with a small amount of material that barely covers the surface of the sieving membrane. Accordingly, the products, systems, and methods of the invention beneficially provide superior sieving performance, including increased sieving speed, as well as improved particle distribution across the surface of a sieve and/or a test coupon. In further aspects, the present invention utilizes a dust storm generating apparatus and method to evenly distribute particles. Once an even distribution of particles deposited on a substrate has been achieved, additional apparatus and methods may be used to directly select and deposit particles of interest on substrates in desired patterns.

The invention described herein, including the various aspects and/or embodiments thereof, meets the unmet needs of the art, as well as others, by providing a method and apparatus to deposit small solid particles of a known chemical through a sieve, or using a dust storm technique, onto one or more coupons in a controlled fashion to produce a more uniform distribution and loading of particles on each coupon. In the case of a sieving method and apparatus a more uniform distribution of particles across the sieving membrane may also be achieved.

This invention enables the processing of solid micron-sized particles for rapid deposition on substrate surfaces with a substantially uniform particle distribution. The invention expands the practical range of sieve mesh openings to below 20 microns, allowing particle fractionations of different size ranges between 0-20 microns, including but not limited to 10-20 microns, 5-15 microns, and 0-10 microns. This is of particular importance for fabricating test specimens to be used in analytical applications, such as trace particle detection of explosives or environmental pollutants.

The sieving apparatus and methods of the invention may be beneficially used in conjunction with controlled particle deposition techniques in which particles deposited on a test coupon are individually selected for further processing.

According to a first aspect of the invention, a sieving apparatus is provided, including a sieving pan adapted for receiving particles to be sieved, which includes a sieve membrane having upper and lower surfaces and a wiper that wipes particles over an upper surface of the sieve membrane. The sieving apparatus further includes a collection pan that retains particles that pass through the sieve membrane, and a substrate provided within the collection pan to receive a portion of the particles that pass through the sieve membrane. The wiper is moved with respect to the upper surface of the sieve membrane and applies force to particles adjacent to the upper surface of the sieve membrane, producing particle distributions on the membrane which for a time averaged basis spend an equal time at their prescribed radius from the center of a circular sieve for the corresponding circular path to produce a substantially uniform time averaged distribution of particles across the membrane at the width of the wiper and accelerating the movement of the particles through openings in the sieve membrane into the collection pan and onto one or more substrates.

According to another aspect of the invention, a sieving apparatus is provided, including a sieving pan adapted for receiving particles to be sieved, which includes a sieve membrane having upper and lower surfaces. The sieving apparatus further includes a collection pan that retains particles that pass through the sieve membrane, a rotating coupon stage having a surface adapted to receive one or more coupons, where the one or more coupons receive a portion of the particles that pass through the sieve membrane, and a vibration generator that generates vibratory action to cause particles to pass through the sieve membrane. The coupon stage is provided in the collection pan, and is rotated as the particles are sieved, producing particle distributions that are more uniform across the one or more coupons when compared to particle distributions produced on coupons that are not rotated during sieving.

Another aspect of the invention relates to an apparatus for generating a particle storm, including a container having an opening to introduce a particulate substance therein, a fan apparatus provided within the container, one or more coupon substrates positioned within the container, and a cover for sealing the opening of the container. The fan apparatus is actuated to cause particles within the container to form a particle storm, which deposits particles onto the one or more coupon substrates.

According to a further aspect of the invention, an apparatus for generating a particle storm is provided, including an acoustic transformer configured to generate ultrasonic frequencies, a substrate holder for positioning a substrate having particles deposited thereon adjacent to the acoustic transformer, and a platform for positioning one or more coupons adjacent to the substrate having particles deposited thereon. The acoustic transformer is actuated to cause particles deposited on the substrate to be released from the source substrate and form a particle storm, wherein the particles present in the particle storm are deposited onto the one or more receiving coupons.

According to a still further aspect of the invention, a particle printing apparatus is provided, which includes a first movable stage adapted to hold a first source substrate having particles deposited thereon, an imaging system adapted to record a map comprising locations of particles deposited on the first source substrate, a second movable stage adapted to hold a second substrate designated for receiving particles deposited on the first substrate, and a laser. A particle of interest deposited on the first source substrate is selected using the map recorded by the imaging system, the first movable stage is moved to align the particle of interest with a beam from the laser, second movable stage is moved to align the particle of interest with a location on said second substrate where the particle of interest is to be deposited, and the laser is energized, causing the particle of interest to be dislodged from the first substrate and fall onto the location on the second substrate.

In accordance with another aspect of the invention, a method for sieving particles is provided, including placing particles into a sieving pan including a sieve membrane having upper and lower surfaces and a wiper that wipes particles over an upper surface of the sieve membrane, actuating a vibration generator to generate vibratory action to cause particles to pass through the sieve membrane, actuating a wiper to move across the upper surface of the sieve membrane and apply force to particles on the upper surface of the sieve membrane, producing particle distributions that are substantially uniform across the width of the wiper and accelerating the movement of the particles through openings in the sieve membrane, and collecting particles that pass through the sieve membrane in a collection pan having a substrate provided therein, wherein a portion of the particles that pass through the sieve membrane are deposited on the substrate.

According to a further aspect of the invention, a method for sieving particles is provided, including placing particles into a sieving pan comprising a sieve membrane having upper and lower surfaces and a wiper that wipes particles over an upper surface of the sieve membrane, actuating a vibration generator to generate vibratory action to cause particles to pass through the sieve membrane, actuating a rotating coupon stage having a surface adapted to receive one or more coupons, where the one or more coupons receive a portion of the particles that pass through the sieve membrane as the coupon stage rotates producing coupons having particles deposited therein, wherein the particle distributions on the coupons are substantially uniform, and collecting particles that pass through the sieve membrane but are not deposited on the coupons or coupon stage in a collection pan.

According to a still further aspect of the invention, a method for depositing particles using a particle storm is provided, including providing a particulate material in a container through an opening therein, providing a fan within the container, positioning one or more coupon substrates within the container, sealing the opening of the container, and actuating the fan to generate a particle storm, causing particles in the particle storm to be deposited onto the one or more coupon substrates.

According to yet another aspect of the invention, a method for depositing particles using a particle storm is provided, including providing a particulate substance on a source substrate, placing the substrate having the particulate substance thereon adjacent to an acoustic transformer configured to generate ultrasonic frequencies, placing one or more coupons adjacent to the substrate having the particulate substance thereon, and actuating the acoustic transformer, causing the particulate substance on the substrate to be released from the substrate forming a particle storm, wherein the particles present in the particle storm are deposited onto the one or more coupons.

According to still another aspect of the invention, a method for printing particles onto a substrate is provided, including providing a first substrate having particles deposited thereon on a first movable stage, recording an image comprising sizes and locations of particles deposited on the first substrate, providing a second substrate for receiving particles on a second movable stage, selecting a particle on the first substrate to be deposited on the second substrate using the image, moving the first stage to align the location of the selected particle on the first substrate with the location of a laser beam, moving the second stage to align the location on the second substrate where the selected particle is to be deposited with the location of the selected particle on the first substrate, and energizing the laser beam, causing the selected particle to be dislodged from the first substrate and fall onto the location on the second substrate where the particle is to be deposited.

Test coupons loaded with particles produced using any of the apparatus or methods of the invention are also provided in accordance with the invention.

The invention is further directed to the use of any of the apparatus of the invention to produce a test coupon loaded with particles.

The invention also relates to the use of a first substrate prepared using any of the apparatus or methods of the invention in the particle printing apparatus and method.

Other features and advantages of the present invention will become apparent to those skilled in the art upon examination of the following or upon learning by practice of the invention.

BRIEF DESCRIPTION OF THE DRAWINGS

In FIG. 3A, the coupon platform is contained within the collection pan. In FIG. 3B, a rotating coupon platform and extension sleeve are depicted.

FIG. 9A is a wiper having a blade. FIG. 9B is a wiper comprised of multiple blade segments. FIG. 9C is a wiper having a brush.

FIG. 14A is a container housing a fan and a substrate. FIG. 14B is a view of the inside of the container lid showing a substrate platform mounted therein. FIG. 14C is a view of the substrate platform and substrate.

FIG. 17A shows an inverted image using a 5× objective lens of a glass coupon coated with DNT particles deposited using the dust storm technique. FIG. 17B shows an inverted image of 20 micron TNT particles deposited at a density of 6.0 micrograms/cm$^2$ using a sieving technique. FIG. 17C shows sieved RDX particles deposited onto a substrate containing pools of sebum oil.

DETAILED DESCRIPTION OF EMBODIMENTS OF THE INVENTION

Figure 1:
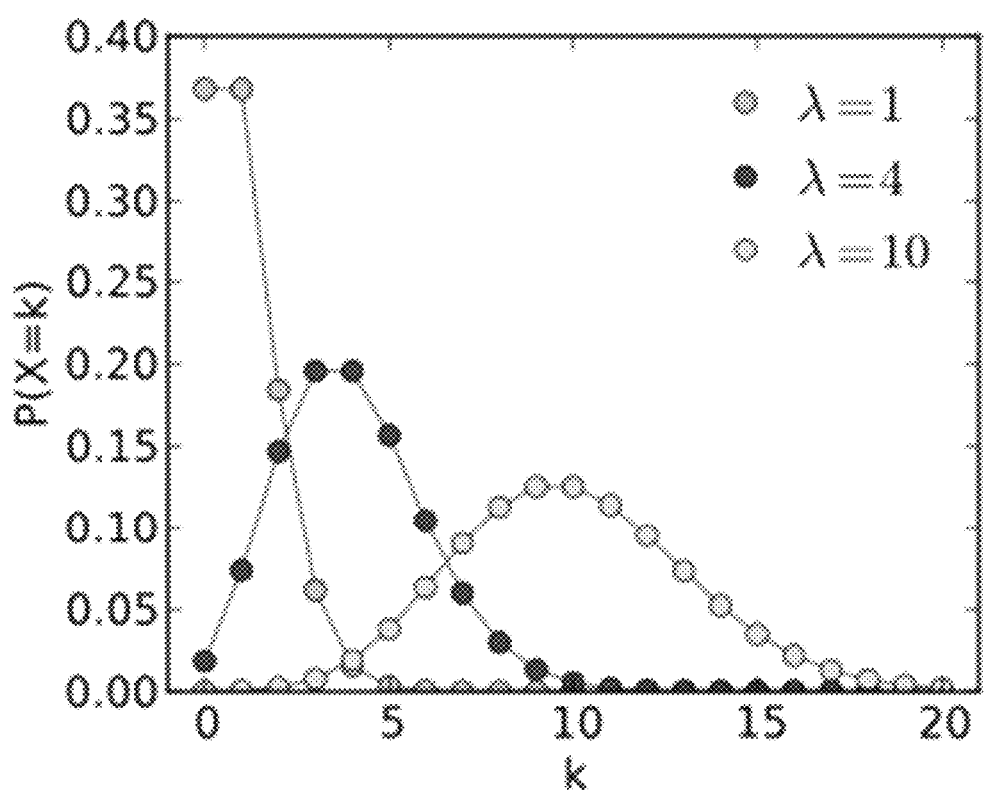
FIG. 1 is a graph illustrating the Poisson distribution when the average number of particles in a given area is 1, 4, or 10.

The invention described herein, including the various aspects and/or embodiments thereof, meets the unmet needs of the art, as well as others, by providing a method and apparatus for depositing particles through a sieve, or using a dust storm technique, onto one or more coupons or substrates. The deposition is controlled in order to produce a substantially uniform distribution of number of particles, areal density and particle size over the intended area on a coupon substrate. The application further relates to a method and apparatus for transferring individual or clusters of particles deposited on a coupon to a different substrate for further evaluation.

The particles processed in accordance with some embodiments of the invention may be microspheres or arbitrary-shaped particles of any organic or inorganic chemical. Of particular interest are explosives or narcotics or related materials.

The explosives or explosive-related materials encompass organic and inorganic materials, and may include, but are not limited to, 2,4,6-trinitrotoluene (TNT), triacetone-triperoxide (TATP), octahydro-1,3,5,7-tetranitro-1,3,5,7-tetrazocine (HMX), ammonium nitrate (AN), potassium nitrate (KN), urea nitrate (UN), potassium perchlorate (PP), potassium chlorate (PC), octahydro-1,3,5,7-tetranitro-1,3,5,7-tetrazocine (HMX), hexahydro-1,3,5-trinitro-1,3,5-triazine (RDX), and pentaerythritol-tetranitrate (PETN).

The narcotics include, but are not limited to heroin, lysergic acid diethylamide (LSD), marijuana (cannabis), 3,4-methylenedioxymethamphetamine (ecstasy), methaqualone, peyote, Vicodin, cocaine, methamphetamine, methadone, hydromorphone, meperidine, oxycodone, fentanyl, Dexedrine, Adderall, and Ritalin. Drug schedules maintained and updated by the U.S. Drug Enforcement Administration (DEA) classify drugs as Schedule I, Schedule II, Schedule III, Schedule IV, and Schedule V based on their potential for abuse and dependence. Particles comprising drugs selected from any of these schedules may be used in the apparatus and methods of the invention. In some embodiments, the particles comprise DEA Schedule I or Schedule II substances.

Particles processed in accordance with some embodiments of the invention may be taken from visible, UV or infrared dyes, and polymers including, but not limited to polystyrene, polyacrylonitrile, polyethylene, polymethylmethacrylate, polyvinylchloride, nylon, Teflon, polyurethane, polypropylene or silica.

Particles of materials found in chemical and biological weapons may also be processed by the apparatus and methods of the present invention including, but not limited to, chemical nerve and blister agents formulated in porous or adsorbent solid particles or with binder materials with solid properties, ricin, bacillus anthracis, botulin toxin, francisella tularensis.

Environmental pollutants may also be processed using these methods and apparatus including, but not limited to, pollen, mold spores, bacteria, cement dust, fly ash, oil smoke particles, tobacco smoke particles, soot, and carbon black.

The particles may also be selected, without limitation, from narcotics, pharmaceuticals; cosmetics; cement materials; components used in inks; food substances including sugar and flour; cosmic or "space" dust, and other particulate matter derived from comets, asteroids, meteroids; contaminants of any of the materials described in this application; and any other compositions that are supplied or may be detected in powder or particulate form.

In accordance with other aspects of the invention, the particles used in the sieving and dust storm techniques are preferably solid (i.e., have a fixed shape and volume). Although the particles deposited by dust storm are not particularly limited, they preferably range in size from about 1 to about 100 microns, preferably from about 3 to about 50 microns, and more preferably from about 5 to about 30 microns. Preferably, the particles do not exhibit significant levels of clumping or agglomeration (i.e., less than about 50% of the particles are clumped/agglomerated, preferably less than about 25%, more preferably less than about 10%, and still more preferably less than about 5%), which in some aspects may be related to the moisture content of the particles. The particles may have a moisture content that is less than about 25% by weight, preferably less than about 10% by weight, more preferably less than 5% by weight. In some aspects, the moisture content is approximately 0% by weight, and may be achieved by any drying technique that does not alter the shape or size of the particles.

The ideal particle size and shape is determined by the application and the need to fabricate representative samples with corresponding particle sizes and spatial coverage. For security applications which relate to depositions of particles within fingerprints, a range of particle sizes are crushed and deposited with a typical range (comprising 75% of the particle mass) being from 1-25 microns in diameter. To avoid particle aggregation in the sieve pan, dry particles and a dry atmosphere is preferred. As the size of the desired particles decreases it becomes increasingly difficult to sieve through smaller sieve meshes. This is particularly marked for sieve meshes with openings with dimensions less than 10 microns. The dust storm technique is not restricted by any sieve mesh opening size and may be applied to any size range of interest between 1-100 microns.

In accordance with the invention, coupons or test coupons are substrates having surfaces designed to receive the distributed particles thereon, and may be provided in any shape or size desired. For example, square coupons that are 1" by 1" are preferred in some aspects of the invention. The coupons are preferably formed from a material that exhibits little or no reactivity with the deposited particles. In some aspects, it is permissible for the substrate to interfere with the functioning of the detection equipment that may be used to detect the deposited particles, in which case the detection equipment separates signals from the target analyte from signals from the substrate, for example, using an algorithm. Exemplary materials for use as test coupons include glasses used in consumer electronics or automobile applications. Silicate glasses, such as soda lime glass and borosilicate glass, may be used. A wide range of polymers may also be used in accordance with the invention, such as polymethacrylate, polystyrene, Bakelite, polyvinylchloride, nylon, polyethylene terephthalate, polyurethane, polycarbonate, or polyethylene. Metals, painted metals, wood, paper, cardboard, and woven cloth may also be used as test coupons.

In one embodiment, the test coupon material is formed from a substrate material that exhibits minimal or no reactivity with the particles deposited thereon. However, in other embodiments it may be desirable for the particles to interact with the surface of the coupon or substrate, for example, to cause the deposited particles to adhere to the surface with the characteristic forces or bonding present, including but not limited to covalent bonding, ionic bonding, hydrogen bonding, Van der Waals forces, and capillary action of a co-located liquid such as sebum oil. A cover slip may optionally be applied to the particles deposited on the test slip in some aspects of the invention.

An adhesive layer can optionally be applied to the surface of the test coupon and/or a slide cover can be placed on the surface of the coupon after the particles have been deposited therein in accordance with some aspects of the invention. Preferably the adhesive does not alter the properties of the deposited particle, or interfere with the functioning of a detection apparatus used to detect the presence of the deposited particle.

Figure 17A:
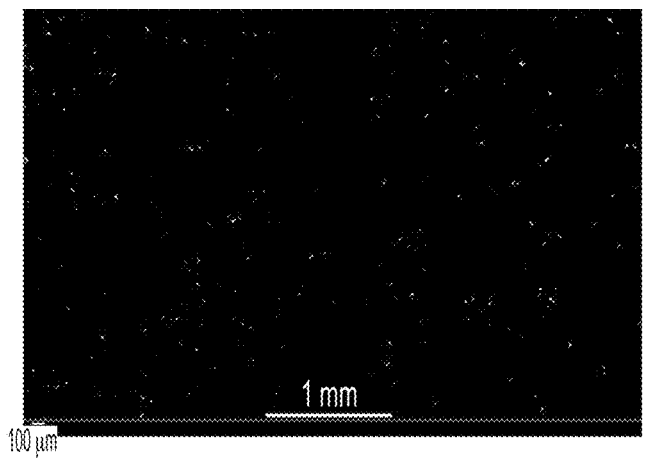
FIGS. 17A-C are photographs of particles deposited using the methods of the invention.
Figure 17B:
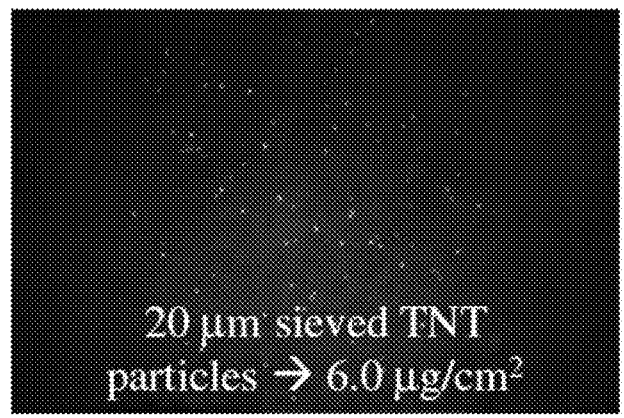
Figure 17C:
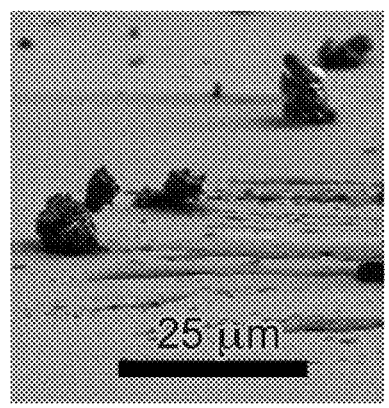

In some aspects of the invention where improving the accuracy of detection of particulate matter in fingerprints or other body parts is important, it may be beneficial to apply a pattern of sebum oil and/or sweat to the coupon prior to or after depositing the particulates. FIG. 17C is a photomicrograph that shows RDX particles deposited onto a substrate containing pools of sebum oil. The sebum and/or sweat may be applied as a layer, or in a manner that mimics contact of a body part with the coupon, for example, full or partial prints deposited by contact with the hands or fingers. The sebum and/or sweat may be deposited by touching the coupon with a body part of interest, or simulated version of a body part, or by using a printing technique that applies background compounds typically found on the body part of interest (i.e., in the case of contact with skin, applying one or more of glycerides, fatty acids, wax esters, squalene, and sterol esters found in sebum; and/or applying one or more of amino acids, proteins, urea, uric acid, lactic acid, sugars, creatinine, and choline found in sweat) that are likely to be present along with the particulate matter being detected. When improving the detection of particulate matter in other deposited background materials is important, conditions may be reproduced using the mechanism responsible for deposition (i.e., by touching the coupon with a finger), or printing techniques using the likely background compositions can be employed. Non-limiting examples may include, without limitation, footprints, tire tracks, respiration, and detection in hair or fibers from clothing. Background compositions likely to be present as a result of these types of contact can be determined using available forensic reference materials.

Regardless of whether sieving, dust storm, or particle printing techniques are used for particle deposition, it is an aim of the invention to provide feedback control during the sieving, dust storm, or printing process to halt particle deposition when a desired target loading has been achieved. Such feedback control may be accomplished by using optical sensors, weight sensors, or any other type of sensor capable of detecting the presence of particles on the coupon(s) and transmitting the information to a controller or processor used to monitor the particle deposition.

Further, it is the aim of the invention to allow smaller particles of interest to be deposited and fractionated (for example, particles ranging in size from 0 to 10 microns, 5 to 15 microns, 10 to 20 microns or 0 to 20 microns) in a dry atmosphere, which may aid in preventing particles from aggregating prior to deposition, or absorbing water if they are deliquescent, which may cause them to dissolve or otherwise no longer be in a solid form. The dry air supply conditions the air inside the sieving stack or dust storm apparatus, or in the environment where particle printing occurs. This permits more efficient deposition of particles, particularly for particles having dimensions of less than 20 microns, and generally improves sieving control for all particulate materials. For hydrophilic or hygroscopic materials, dry air conditioning within the sieving stack or dust storm apparatus, or in the environment of the particle printing apparatus, is particularly beneficial. The dry atmosphere may have a relative humidity of less than 30% at the temperature being used to process the particles. Preferably, the atmosphere has a relative humidity of less than 20%, more preferably less than 15%, most preferably less than 10%. In some aspects, the atmosphere has less than 5% relative humidity at the temperature being used to process the particles, preferably approximately 0% relative humidity. In order to accomplish this level of dryness, the container used to hold the material being sieved or subjected to a dust storm or printed may be equipped with a valve to permit dry air to be fed into the container volume, and optionally the container may be equipped with a desiccant material to aid in absorbing any residual water vapor present in the container or contributed by the particulate material.

The air to be introduced into the sieving or dust storm apparatus may have a specific temperature, where the temperature may be selected so that the particles of interest remain solid and/or non-reactive and the effects of any residual moisture are limited. Room temperature air is preferred in some aspects of the invention, but it is also envisioned that certain particles may benefit from the use of chilled or heated air. The air temperature may be selected based on the particles of interest, and may be adjusted to ensure that the particles remain solid and non-reactive, or to cause them to become more reactive.

The sieving and dust storm deposition techniques of the invention deposit particles in a random fashion. Therefore, the amount of deposited particles on two sample coupons (or different areas of the same coupon) cannot be exactly the same. The terms "uniform," "similar," "comparable," and "reproducible," when used with respect to the particle deposition achieved by the apparatus and methods of the invention should be interpreted to mean that the difference between the amount of particles deposited on a first sample coupon and a second sample coupon is within the values expected by statistics.

The number of particles randomly deposited in a given area is governed by the Poisson distribution. The probability that a given number of particles will be deposited in a given area is:

$$p(N) = e^{-\langle N\rangle}\frac{\langle N\rangle^k}{k!}$$

where <N> is the average number of particles expected to be deposited.

The average number of particles expected to be deposited is determined by the average mass loading, area of sample, and average particle mass:

$$\langle N\rangle = \frac{\mu A}{\langle m\rangle}$$

For example, if the average number of particles in a given area is only 1, there is a ~37% probability that the area will remain empty and a ~63% probability that the area will be populated with 1 or more particles. The resulting Poisson distributions when the average number of particles in a given area is 1, 4, or 10 are shown in FIG. 1. By increasing the observation area (for the same areal mass loading), this variation decreases.

For larger numbers of particles, the average variation in the number of particles in a given area can be best described by the square root of the variance of the Poisson distribution, which can then be interpreted as the standard deviation of an equivalent normal distribution:

$$\sigma \approx \sqrt{\mathrm{Var}(P)} = \sqrt{\langle N\rangle}$$

In this case, we can state that there is 68.3% probability that the observed (deposited) number of particles is in the range:

$$\langle N\rangle - \sqrt{\langle N\rangle} < N_{observed} < \langle N\rangle + \sqrt{\langle N\rangle}$$

It is important to note that as the number of particles grows, the relative deviation in the number of deposited particles decreases and is given by:

$$1/\sqrt{(N)}$$

Any deposition that has a deviation in particle numbers between two areas that is (substantially) greater than given by the above two equations can be considered to be "non-uniform," "not reproducible," "dissimilar," or "not comparable." The sieving and dust storm apparatus of the invention may be beneficially used to avoid non-uniform particle deposition.

When the terms "uniform distribution" and "substantially uniform distribution" are used in accordance with the various embodiments of the invention, it is understood that for areal densities of particles ranging from 0.01 to 200 micrograms/cm$^2$ provided on the coupon or substrate in the desired areas as a result of using the apparatus and methods of the invention, the areal density on average varies by less than 100% in the target region coated. Preferably, the particle areal density varies by less than 50% in the target region coated. More preferably, the particle loading areal density varies by less than 10% in the target region coated. Most preferably, the particle loading areal density varies by less than 3% in the target region coated. The loading may be non-uniform in accordance with some embodiments of the invention, for example, a particular desired particle loading may be achieved in a smaller target area within the deposition surface area by use of a mask or other means for limiting particle deposition to a target area, where the remaining surface area outside the target area contains no particles. It is understood that the desired areal density and aerial density uniformity of the particles varies depending on the relevant application and the particle type being deposited, and the nature of the further analysis to be conducted using the particles. For example, in order to fabricate test coupons to mimic particles deposited in a fingerprint it is desirable to control particle depositions in a heterogeneous fashion with small islands of particles with relatively high areal densities.

One preferred embodiment of the invention deposits small solid particles through a sieve, or using a dust storm technique, or by direct particle printing, onto one or more coupons in a controlled fashion in order to produce a reproducible average distribution of particles on each coupon in a targeted area. One or more test coupons may be monitored as a way of assessing the particle loading over multiple coupons which are not monitored.

The particle-deposition apparatus and techniques of the invention correct for particle deposition non-uniformities by moving the coupons during particle deposition, randomizing particle movement, or directing deposition on a particle-by-particle basis, thereby avoiding exposure to non-uniform deposition conditions. The invention also expands the range of particle sizes that can be uniformly deposited, and in particular allows practical depositions of particles in the 5-20 micron size range when using sieves with comparably-sized openings. These aims of the invention are of particular importance for fabricating test specimens to be used in analytical applications such as trace particle detection of explosives, narcotics, or of other environmental pollutants. The invention may also find applications in formulating or processing pharmaceuticals, cosmetic products, cement materials, inks, and foodstuffs.

Various apparatus suitable for use in carrying out the invention will now be described in connection with the drawings provided herein. The invention will also be described with respect to presently-preferred and exemplary methods for employing the apparatus described herein. The apparatus described herein are not to be construed as limited to use in any particular methods, and the methods are not to be construed as limited to any particular apparatus, and neither are to be construed as limited to the detection of any particular particles or substrates of interest. It is to be understood that the various embodiments discussed below are not intended to be limiting, and that alternative configurations and techniques are envisioned based on these exemplary apparatus and methods that achieve the desired particle processing.

Sieving.

The sieving apparatus and techniques in accordance with the invention may preferably be based on a vibration generator that generates vibrations, such as a shaker apparatus. The vibration generators of the invention include, but are not limited to, shakers such as the Gilson Performer III sieve shaker platform (manufactured by the Gilson Company, Inc., of Lewis Center, Ohio). Shakers may incorporate electromagnetic vibratory action with amplitude and timer control, and optionally provide impact hammer tapping action to reduce clogs in the sieve mesh.

Figure 2:
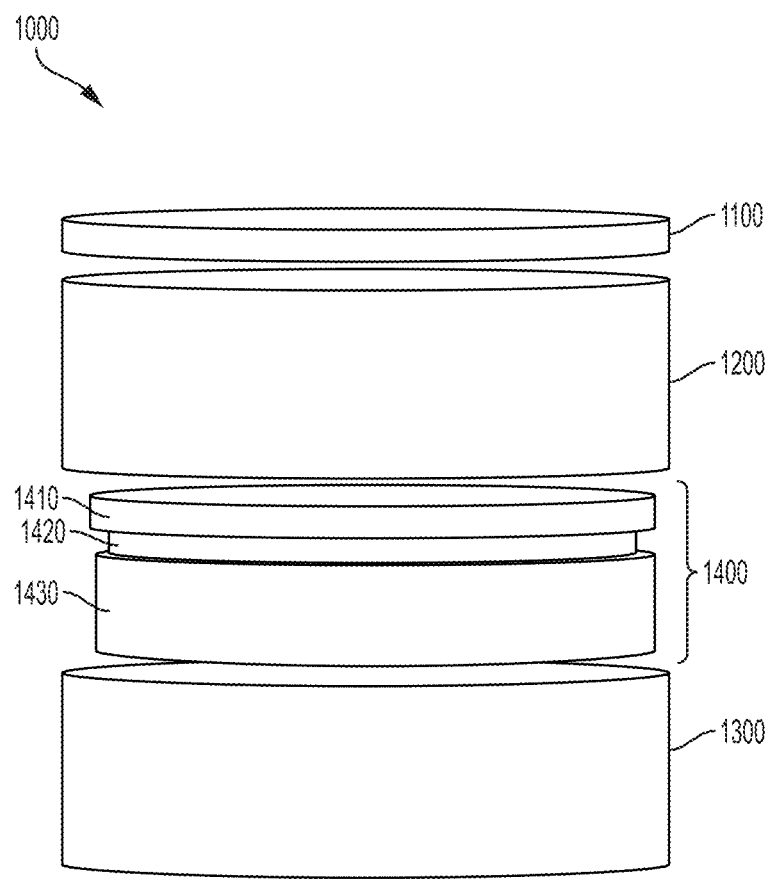
FIG. 2 is a drawing depicting a sieving stack.

An outside view of a sieving stack 1000 that may be used to achieve particle sieving is illustrated in FIG. 2. The sieving stack 1000 includes an upper lid 1100 that covers a sieving pan 1200. The sieving pan 1200 sits above a collection pan 1300, which may include a substrate holder 1400 therein. The substrate holder may include a mask 1410, a substrate upon which particles are to be deposited 1420, and a substrate holder or platform 1430.

Additional variations in sieving stacks in accordance with the invention are illustrated in FIGS. 3-9.

Figure 3A:
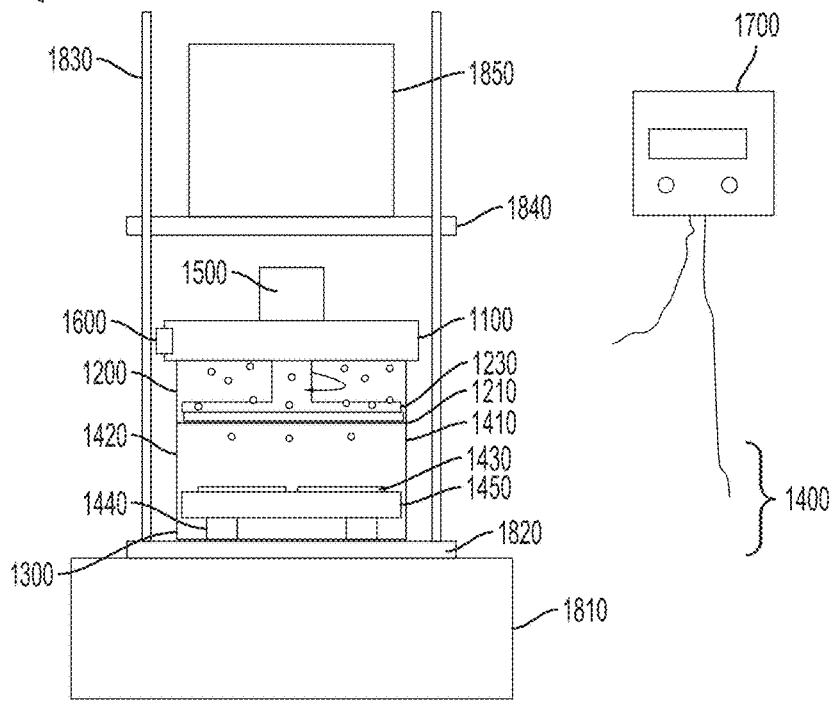
FIGS. 3A and 3B are drawings of sieving stacks installed on a shaker platform, with an impact hammer provided above the sieving stack lid.
Figure 3B:
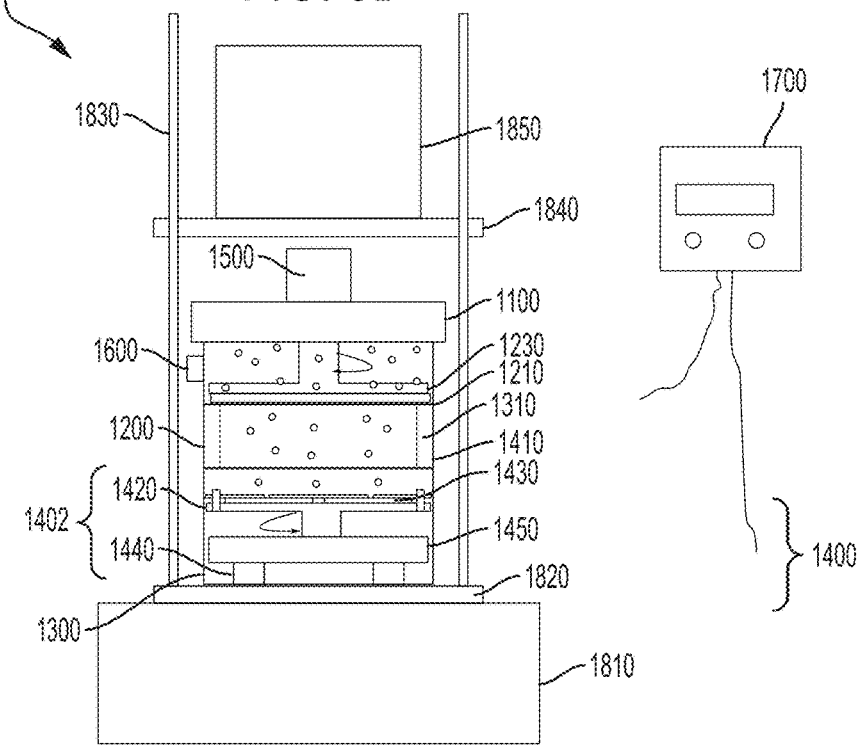

FIGS. 3A and 3B depict embodiments of a preferred sieving apparatus in accordance with the invention. In FIG. 3A, a shaker apparatus 1800 is depicted with a sieve stack 1000 affixed thereto. Shaker 1810 includes a vibration plate 1820 thereon, and the vibration plate 1820 includes support rods 1830 that extend up in order to securely support the sieve stack 1000 and transmit vibration throughout, as well as permit a striker plate 1840 and striker 1850 to be mounted above the sieve stack. The striker plate 1840 may be impacted by the striker 1850 during sieving to prevent sieve blockages and irregularities in particle distribution from occurring. The sieving stack includes lid 1100 having an optional air inlet port 1600 provided therein (in some aspects, such as the one depicted in FIG. 3B, the air inlet port 1600 may be provided in the side wall of the sieving pan). Sieving pan 1200 includes a sieving membrane or mesh 1210, and may also include a wiper or blade 1220. When wiper 1220 is provided, a motor 1500 may be provided to drive rotation of the wiper 1220 over sieve membrane 1210, further improving the distribution of particles across the surface of the sieve and speeding sieving time.

Any particles that are able to pass through the sieve fall into collection pan 1300, which holds substrate/coupon holder 1400. The coupon holder 1400 has a mask 1410 provided on an upper surface thereof, which exposes only the portion of the coupon 1420 upon which particles are to be deposited. The coupons 1420 are placed in a coupon platform 1430 that may be outfitted with a vibration damper 1440. The coupon holder 1400 may be configured to rotate in order to prevent irregularities in particle deposition across the coupons 1420, and a rotating coupon holder 1402 is shown in FIG. 3B. All motors and actuators used in the sieving apparatus, as well as the shaker, may be controlled using a controller 1700, which may be programmed to vary the intensity of shaking, the frequency of striking, the airflow, the speed and direction of rotation of the sieving blade, and the speed and direction of rotation of the coupon platform. In some aspects, the programmed controller may adjust these or other variables based on direct user input. In other aspects of the invention, the controller adjusts variables based on detection of blockages on sieve membranes, and the weight and distribution of particles detected on one or more coupons.

FIG. 3B depicts an extension sleeve 1310 incorporated between the sieve pan 1200 and the collection pan 1300. When provided, the extension sleeve 1310 provides additional clearance for the coupon holder 1400, which may be particularly useful when a rotating coupon platform 1402 is provided to support the coupons 1420.

Figure 4:
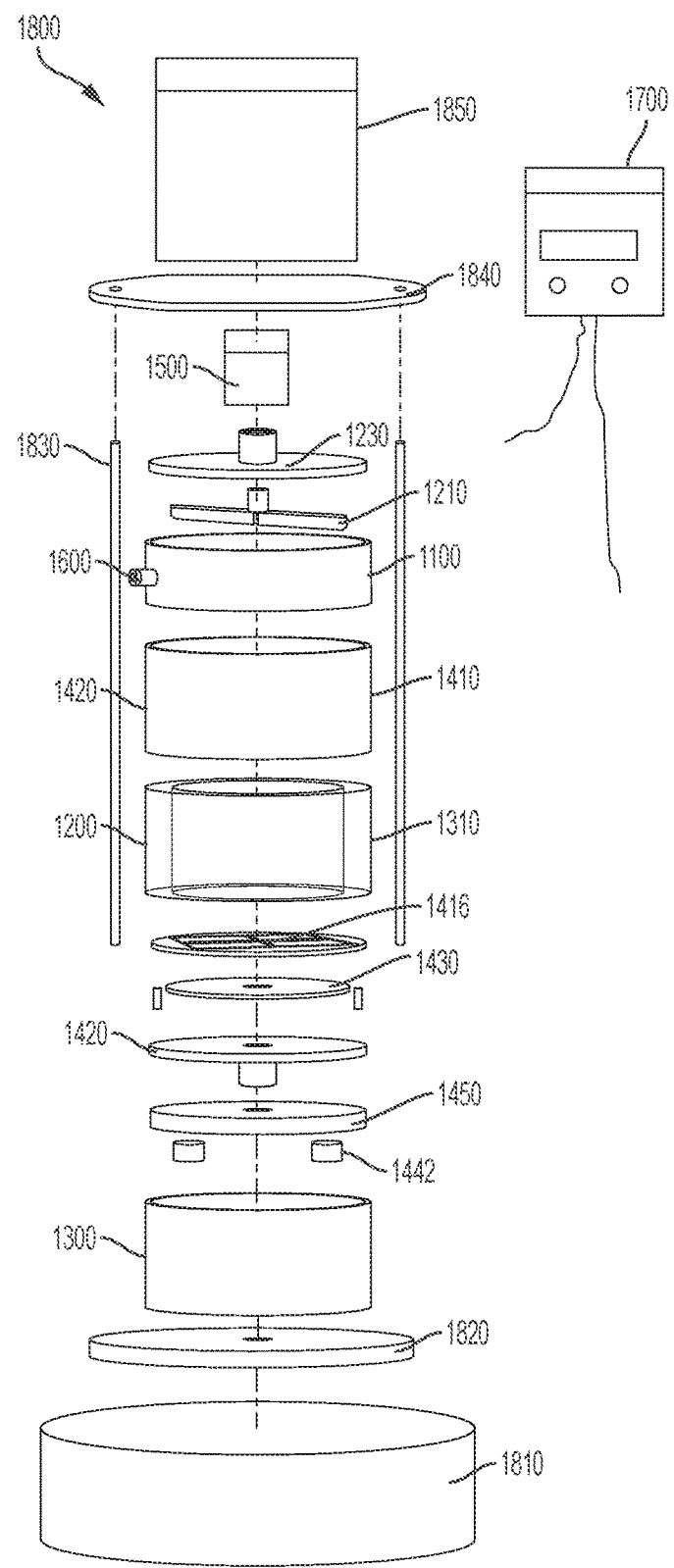
FIG. 4 is an exploded view of a sieving stack and shaker platform with support structure.

FIG. 4 is an exploded view of the elements of the sieving apparatus as shown in FIG. 3B.

Sieving stacks may be based on one or more sieving pans that are arranged by stacking them, and where more than one sieving pan is provided, they are preferably stacked in order (from top to bottom) so that the sieve with the mesh that permits the largest particles to pass through is provided at the top, and the sieve with the mesh that permits the next largest particles to pass through is in the middle, and the sieve with the mesh that permits the smallest particles to pass through is provided at the bottom. Such an arrangement may provide more efficient sieving while avoiding clogged mesh. The one or more sieving pans are stacked on a collection pan, which captures the particles that are able to fall through the sieve or sieves. Conventional or commercially-available sieving stack components may be used in accordance with the invention, incorporating one or more of the modifications described herein.

In some embodiments of the invention, the sieve may be formed using a metal mesh or fabric. Non-metallic mesh or membrane may also be used in accordance with the invention, and such sieves may be formed, for example, from polymers such as polyester or nylon. The mesh size of the sieve may range from 2500 mesh (5 microns) to 35 mesh (425 microns), preferably from 1250 mesh (10 microns) to 60 mesh (250 microns), more preferably from 800 mesh (15 microns) to 60 mesh (250 microns), and most preferably from 625 mesh (20 microns) to 200 mesh (75 microns). In some aspects, it is preferred that the mesh size be selected to allow for effective sieving of particles ranging from 1 to 20 microns in size, i.e., from 2500 mesh to 625 mesh. It is understood that sieving membranes will permit particles corresponding to the given mesh size or smaller to pass through the sieve for deposition onto the coupon or substrate. In some embodiments, in order to increase particle uniformity, the particles may be pre-screened one more times to remove particles that are less than a designated size. Particles may also be ground using a mortar and pestle (automated or not), or milled (for example, using a ball mill) before being used in the sieving apparatus and methods of the invention. Such pre-deposition processing may beneficially improve the consistency and size uniformity of the deposited particles. The composition of the sieving membranes used in accordance with the invention may be varied as long as they achieve the desired level of sieving efficiency and uniformity of particle distribution.

Sieving Under Dry Conditions.

Processing particles in a dry atmosphere generally reduces particle agglomeration in the sieving pan, allowing improved sieving particle throughput via sieve openings and onto coupons positioned below the sieve. Sieving techniques including shaking the entire sieving stack and applying periodic impulse strikes to the top of the stack using a striker may be employed to reduce agglomeration. It has been found that the use of dry air further improves particle processing, and may be preferred where the particles are prone to agglomeration.

Figure 8:
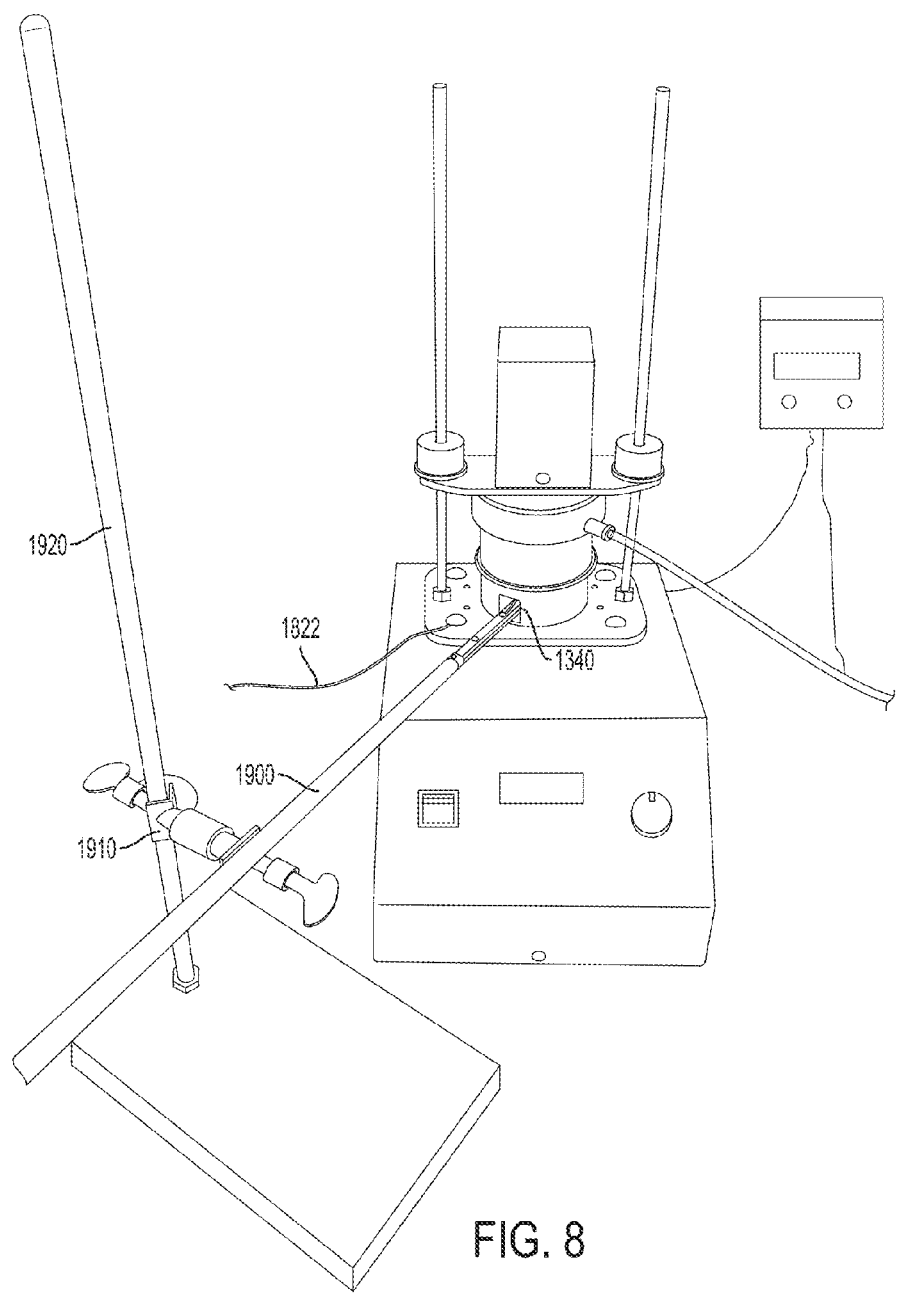
FIG. 8 is a drawing of a sieving stack provided on a shaker with a separate vibration isolating arm holding a coupon platform, and a separate stand for mounting the arm.

In order to provide a dry air supply to the sieve stack, the lid of the sieving stack or the side of a sieving pan may be modified to provide an attachment point for the dry air supply. Mounting the air valve on the side of the lid or sieving pan beneficially avoids direct airflow onto the particles resting on the mesh of the sieve, thereby avoiding undesirable airflow redistribution of particles positioned on the sieving mesh. Various configurations for sieving stacks that include the dry air supply 1600 are shown in FIGS. 3A, 3B, and 4. (The use of dry air supply 1600 with attached air inlet tube 1610 is shown in FIG. 8.)

In some aspects, conditioning the air for zero humidity allows particle sieving through mesh sizes with openings of less than about 20 microns. Sieving with a 10 micron sized mesh under zero percent relative humidity is possible using this optional sieve stack modification. Sieving under zero percent relative humidity can be included as part of a standard protocol in some embodiments. An initial preconditioning of particles in the sieving pan(s) ("drying time") is sometimes desirable prior to the initiation of the actual sieving process in order to ensure that the material to be sieved is completely dry. For some materials, it is also helpful to precondition the particles under 0% relative humidity during any procedures leading up to loading the sieve pan. This optional aspect of the invention can be achieved, for example, in a glove box with a dry atmosphere. To maintain the low or no humidity atmosphere, desiccant materials may be placed in the sieve stack in locations where they are not likely to interfere with sieving or impact particle distribution, such as on the underside of the sieving pan lid, or on the side of the sieving or collection pans in a location that does not impede rotation of the sieving blade or rotating coupon platform, if provided.

Coupon Holder.

To avoid contamination or agglomeration, it is desirable to catch the sieved particles as they fall through the lowest sieving pan before they contact the collection pan. One or more glass coupons may be positioned in the collection pan to receive the particles. In one aspect of the invention shown in FIG. 5, a coupon holder or substrate holder 1400 is provided in a collection pan 1300, which may include an optional an extension sleeve 1310. The substrate holder 1400 keeps the one or more coupons or collection substrates (not shown) in place during particle deposition.

Additional features may optionally be incorporated into the coupon/substrate holder 1400, for example, to improve uniformity of particle deposition on the coupons. In some aspects, a mask 1410 is provided to control the area of the coupon upon which particles may be deposited. The coupon holder can incorporate a substrate platform 1430 that incorporates recesses 1432 to house gaskets 1434 that mate to the coupons in order to keep the coupons secure while sieving is performed, and to relieve any stresses applied to the coupons when the optional coupon mask 1410 is secured to the coupon holder. The recesses in the coupon holder can be adapted to accommodate different coupon sizes or shapes.

It should be appreciated that different sieve sizes and different coupon sizes may be selected so that a smaller or larger number of coupons can be coated simultaneously. Coupon substrates may be provided in any size, but are preferably square, and more preferably are square with dimensions of 1 inch×1 inch. For a typical 3-inch diameter commercially-available sieve pan, this allows four coupons to be simultaneously coated during the sieving operation.

The main functionality of the coupon gasket 1434 is to gently press the coupon against the mask 1410 and keep the coupon in position. By design, a coupon only contacts the gasket at its outer edges to limit any possible contamination from the gasket (e.g. monomer or plasticizer bleed from the gasket). According to some aspects, a harder or more dense gasket (e.g., a gasket made from Dragon Skin® 20 silicone rubber, manufactured by Smooth-On, Inc., of Macungie, Pa.) may be easier to separate from glass coupons than softer or less dense gaskets (e.g., a gasket made from Ecoflex®00-30 silicone rubber, manufactured by Smooth-On, Inc., of Macungie, Pa.).

Figure 5:
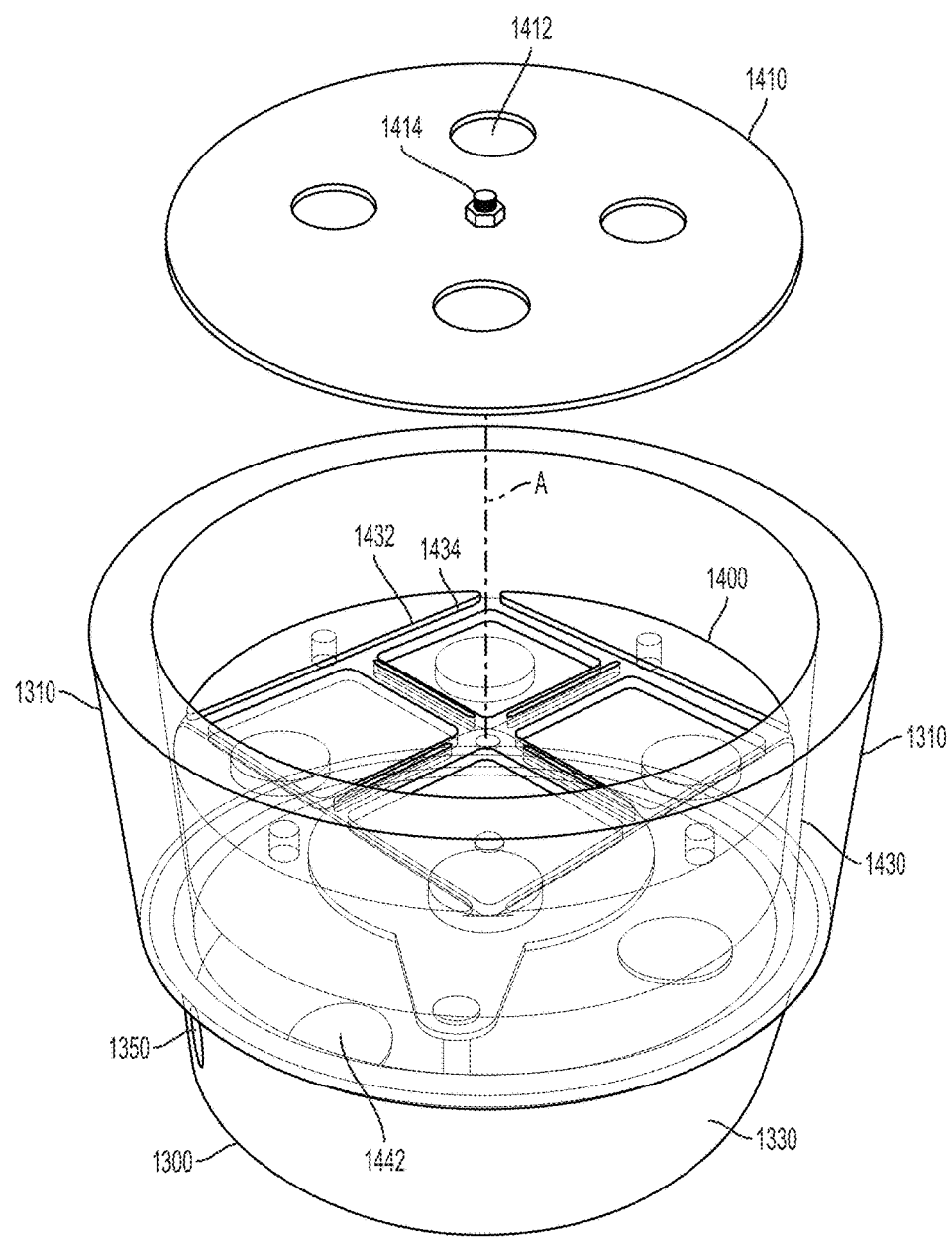
FIG. 5 is a side perspective view of a collection pan having a rotating coupon platform mounted therein, including an extension sieve and mask.

In some embodiments, the coupons are covered with a mask in order to control deposition of particles on the coupon surface. The mask design may vary depending on the particular needs of the end user of the coupons. In some aspects of the invention, the design of the coupon holder provides the capability to select from multiple different masks having openings of different sizes and shapes (e.g., circles, ovals, squares, or rectangles of varying sizes), which are not limited in accordance with the invention. One example of a mask 1410 having circular openings 1412 therein is shown in FIG. 5. In some aspects of the invention, the masks are made of metal. Other mask materials may also be used, such as plastics. The mask material is preferably selected so that the mask is rigid enough not to bend while pushing against the coupon, in order to prevent an air gap from appearing between the mask and coupon, which could lead to unwanted particle contamination beyond the areas defined by the mask. The mask may also be designed to be as thin as is practical to avoid particle "shadowing" effects adjacent to the lip of the mask. Although it may be possible in some aspects to taper the edges of the mask openings, it could be counterproductive in certain configurations if doing so permits particles to "roll" onto the coupon and form agglomerations around the edges of the mask opening. The openings of the masks may be machined precisely enough to mount the mask in either orientation without regard to which side is the top and which side is the bottom, and doing so would allow all each of the multiple coupons to be coated in the same masked area as an individual coupon.

Once the coupons are positioned on the gaskets, or below the gaskets in notches in the coupon holder, the mask can be affixed to the top of the coupon holder. Any means of attachment may be used in accordance with the invention, such as screws or clamps (see, e.g., FIG. 5, screw 1414).

Figure 6:
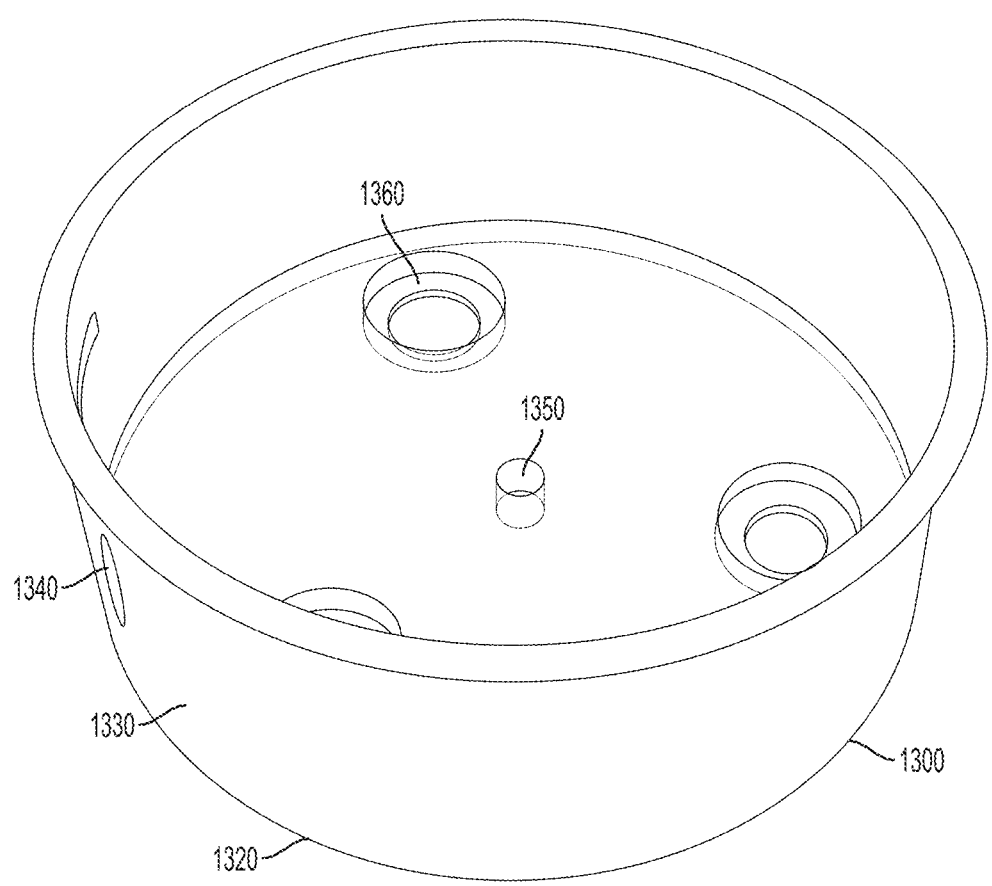
FIG. 6 is a drawing of a collection pan showing recesses to receive damping feet, and showing a conduit hole, and an opening for an arm.
Figure 7:
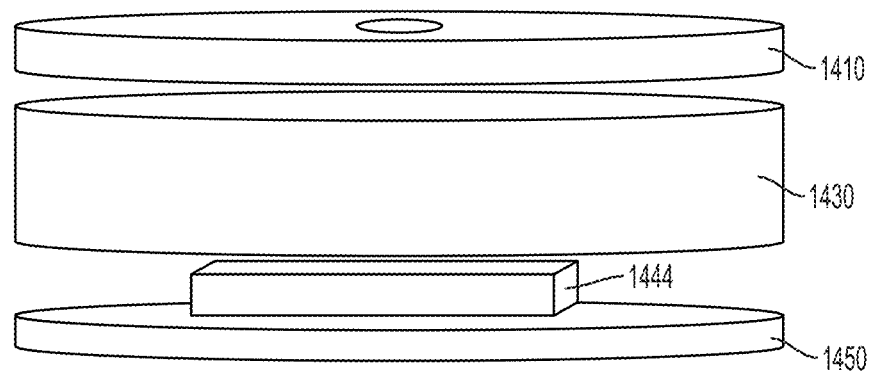
FIG. 7 is a drawing of a coupon holder in which an electromechanical decoupler is provided as a vibration damper.

In one aspect of the invention, a small screw with a lock nut on top (see, e.g., FIG. 4, nut 1416) may optionally be included to enable easy insertion and extraction of the coupon holder from the receiving or collection pan 1300. The coupon assembly may be affixed to the floor of the collection pan 1320 using vibration dampers 1440 that sit in recesses 1360 configured to hold dampers 1440, as shown in FIGS. 5 and 6. This feature helps to maintain alignment of the coupon assembly with respect to the rest of the sieving apparatus, and helps to prevent unintended contact between the wall of the collection pan and the rotating coupon assembly.

The insertion and positioning of the coupon holder in the sieving stack is typically a manual procedure, though automatic means may also be used in accordance with some aspects of the invention. Positioning the coupon holder requires care to ensure the coupon holder does not make contact with the wall of the receiving pan while operating the sieve stack in order to avoid transmitting vibration to the coupons and impacting particle distribution thereon. To simplify the coupon holder insertion into the receiving pan, a ring (not shown) could be used to align the holder within the pan. The inner diameter of such a ring should be large enough to match the diameter of the mask or coupon holder (whichever is larger), and the outer diameter should be small enough to fit into the receiving pan.

In embodiments where the mask is used, the surface area of the sieve is larger than the surface area of the masked area(s) on the coupon(s), which leads to losses of particles during the sieving process. This material may be captured in the collection pan, and if necessary this material can be reclaimed after the sieving is completed.

One or more test coupons used in accordance with the invention may be held in a stationary position in order to allow particles from the sieving apparatus to be deposited thereon. However, in a particle deposition environment with particle flux discontinuities, an uneven distribution across the collection pan or coupons positioned in the collection pan can result if the coupon platform is stationary. To counter this issue, several optional modifications to the coupon platform may be employed individually or collectively in order to assist in averaging or evening out particle deposition patterns.

Rotating Coupon Platform.

In one alternative, the one or more test coupons may be held on a moving coupon platform in order to compensate for any lack of uniformity in depositing particles during the sieving process. Preferably, the moving platform is a rotating platform. The rotation may be generated, for example, by using a windable spring-based mechanism, or a motor. The speed of the moving platform may be controlled manually, or by using a microcontroller attached to the motor. The microcontroller may be programmed to permit a user to vary the rotation speed. Alternatively, the microcontroller may be programmed so that the rotation speed is adjusted automatically based on information regarding the particles (such as density and size), the detection of particle flux non-uniformities, and the loading level of the coupon or coupons, beneficially permitting end result-controlled test coupon fabrication that achieves specific desired particle size and areal coverage parameters.

For example, with respect to the coupon platform shown in FIG. 5, in which a 3-inch diameter circular collection pan 1300 houses an array of four 1 inch square coupons arranged on a coupon holder 1400, a motorized stage 1430 is provided. The coupon holder 1400 may be rotated around a central axis A with a fixed distance between a coupon and the axis of rotation. In other embodiments, a rotating coupon platform may be used where the radius representing the distance between the coupon and the axis of rotation is varied during sieving operations (not shown), further improving system performance with respect to averaging particle flux from the sieve pan to collection pan.

The rotation of the coupon array platform should be fast enough to avoid particle aggregation due to particle flux discontinuities, typically substantially faster than the rotating blade sieving operation, with speeds of 2 to 10 times faster being typical, but not so fast as to cause excessive particle roll when a particle lands on a coupon (driven by centripetal forces) or particle redistribution after surface attachment (or complete detachment) towards the circumference of the collection pan. The rotating coupon platform permits improved particle deposition uniformity, and reproducibility of particle deposition on different coupons. Optimization of rotation speeds and forwards and backwards timed cycles may further improve particle deposition uniformity on loaded coupons.

In one aspect of the invention shown in FIG. 5, an electrical conduit hole 1350 in the sidewall 1330 of the collection pan 1300 provides access for any electrical cabling to power or control the motor. A plug or patch (not shown) may be formed, for example, using tape, epoxy, or any suitable sealing material, and can be used to block any remaining hole not filled by the wires in order to prevent airflow from being channeled through the hole. Another optional location for a conduit hole 1350 is shown in FIG. 6, in which the conduit is provided through the bottom of the collection pan.

As shown in FIGS. 3A, 3B, and 4, a microcontroller 1700 and one or more stepper motors 1500 may be used to control the motor and rotating coupon platform. One exemplary microcontroller that may be used in accordance with the invention is the Arduino® microcontroller from Adafruit Industries, New York, N.Y., though the invention is not limited to any particular microcontrollers or associated software. In-house developed firmware allowed for control of rotating coupon platform functions including: rotation velocity, rotation time duration, rotation direction, continuous or alternating direction of rotation, radius of coupon rotation, and timing synchronization with the Gilson Performer® III3 sieve shaker unit (including both vibration and periodic striking). It will be appreciated that any general purpose controller may be used, and that the controller may be programmed to carry out these or other rotating coupon platform functions.

The height of the coupon assembly and the motorized stage that provides rotation of the coupon assembly may be higher than commercially-available 3-inch diameter collection pans, as shown in FIGS. 3B and 5. In order to connect the collection pan and coupon assembly to the sieving pan, an optional sleeve 1310 may be used to mate the two pans together while allowing sufficient head room below the sieving pan to accommodate the motorized coupon assembly.

Vibration-Isolated Coupon Holder.

One challenge with employing a commercial sieving stack system and the fabrication of an array of particle-coated coupons is the vibration coupling of the sieving stack to the coupons themselves. This can lead to undesirable particle redistribution on the coupons after their initial deposition on a coupon. In some aspects of the invention, this effect may be eliminated or significantly reduced by physically decoupling or isolating the coupon from the collection pan vibration source and/or isolating vibration of the coupons.

Vibration isolation may be achieved according to one aspect of the invention by using an assembly with viscoelastic rubber or foam mounts that form an interface between the collection pan and the coupon assembly. Exemplary mounts are shown in FIGS. 4 and 5, as feet 1442.

According to one aspect of the invention shown in FIG. 6, the coupon holder (not shown) may be decoupled from the vibrating collection pan by providing a conduit hole 1350 in the bottom surface 1320 of the collection pan 1300 (if required for power). This may be achieved through electromechanical decoupling or mechanical decoupling.

The mechanical decoupling may be accomplished using damping, which can be achieved by one or more means including, but not limited to: springs, ball bearings, viscoelastic polymers, and/or foam spacers. These decoupling means all employ the physical property of inertia. As shown in FIGS. 4 and 5, one technique for decoupling vibrations sourced from the receiving pan 1300 to the coupon holder/assembly (not shown) is to use a viscoelastic rubber material to absorb and dissipate the mechanical vibration energy. Coupon holder base 1450 is provided at the bottom surface 1320 of receiving pan 1300, and vibration damper 1440 is formed using multiple rubber feet. The damping accomplished using this approach is maximized when the viscoelastic properties of the rubber material are a suitable match for the vibration frequencies involved. It should be noted that low frequency vibrations are much less likely to displace small particles, as compared to high-frequency vibrations. Accordingly, complete mechanical decoupling is often not necessary in order to use the sieving apparatus of the invention, and carry out the sieving methods of the invention.

FIG. 7 depicts an aspect of the invention in which an electromechanical decoupler 1444 is used to dampen vibrations received through base 1450 so that they are not transferred to substrate platform 1430, which supports the coupons (not shown) and receives mask 1410. Using the electromechanical decoupling approach shown in FIG. 7, the underlying idea is to employ an inertial instrument 1444 that is provided between coupon holder base 1450 and coupon platform 1430 to measure induced movements in the collection pan, and produce a counter movement in the coupon holder to cancel out collection pan-induced movements in the coupon assembly. This approach delivers optimum decoupling results, but is more complicated to implement than a mechanical decoupling approach, especially in view of the compact designs preferred in some aspects of the invention. Comparable systems can be found in stabilization systems for digital cameras or in optical tables. One advantage of a microprocessor-controlled electromechanically decoupled coupon holder is the ability to adapt to different frequencies from a vibration source in real time.

As shown in FIG. 8, vibration isolation may be achieved by separately supporting substrate holder 1400 so that it does not contact collection pan 1300 or sieve pan 1200. This may be accomplished, for example, by affixing the coupon holder to a metal rod 1900 which may be mounted using a clamp 1910 to a fixed support 1920 (such as a ring stand, though other apparatus for providing a secure mount may be provided). The arm or rod 1900 passes from outside the sieving stack into the collection pan 1300 through a hole 1340 in its side wall 1330 without contacting any part of the sieving stack 1000. To keep the hole in the receiving pan 1340 as small as possible, the rod may be removed to place the coupon holder 1400 in the pan 1300, and then the rod 1900 may be attached to the coupon holder 1400, preferably at its base 1450. In order to maximize the effectiveness of this configuration, the coupon holder 1400 should be completely level, and the rod 1900 should not contact the edge of the receiving pan 1300. The rod may be supported, for example, by a ring stand 1920, although in some aspects the rod support is a heavy support, or a support that is separate from the support for the sieve shaker, in order to reduce the impact of vibration transmission through the support surface itself.

Electrically Grounded and Suspended Coupon Holder.

Another possible source for non-uniform particle coverage on coated coupons may stem from electrostatic charging of various sieving stack parts. Resulting electrical fields may force the particles to adopt a flight path from the sieving to collection pan which differs from a natural gravitational fall. To avoid undesirable charging, in some aspects of the invention the sieving assembly may be grounded for all electrically-conductive parts. (See, for example, grounding wire 1822 in FIG. 8 provided on shaker vibration plate 1820.) Such grounding, when used, may also be provided to ground the sieve stack with the sieve and pan, the sieve shaker housing, the ring stand and metal rod (if used), as well as the metal mask used to pattern the particle deposition on the coupons.

Wiper Mechanism.

In some aspects, suspending or decoupling the coupon holder from the sieve shaker, or providing a rotating coupon platform greatly improves the control of the sieving process and the ability to deposit a uniform distribution of particles. However, even when the coupon holder is decoupled from the sieve shaker, or rotates to minimize flux, a degradation in the uniformity of deposited particles can be observed over long durations of sieving (e.g., sieving that occurs over a period of 5-10 minutes or greater). By observing the raw material loaded within the sieving pan (for example, by using a transparent sieving lid, or one or more fiber optic cameras placed inside the sieving pans of the sieving stack), it can be seen that certain areas on the sieve may collect a high concentration of particles while other areas have no visible particles, even when the sieving pan is level. This uneven distribution of particles across the surface of the sieve can lead to a poor uniformity of particles deposited on the coupons. At low loadings in the sieving pan (i.e., loadings that do not cover the surface of the sieve membrane), nodal systems which may develop in the sieving membrane could be the source of this uneven distribution.

Another challenge associated with conventional vibration-driven sieving is the time taken to deposit particles having a size in the range of 5-20 microns through a membrane with 20 micron openings. Depending on the target particle loading on a coupon, the sieving process can take from several minutes up to several hours. In order to accelerate this process and improve the distribution of particles within a sieving pan, a blade or brush may be rotated over the sieving membrane, and may optionally directly contact the sieving membrane. The rotating blade or brush improves the average distribution of particles in the sieving pan, and thus improves the uniformity of distribution of the deposited particles in the collection pan.

The use of the wiper is designed to address these issues, and may provide additional benefits. The sieve wiper may facilitate distributing or spreading the raw particulate material within the sieving pan. The sieve wiper may also force particles, with minimal abrasion, through the sieving mesh. In doing so, the wiper maintains unblocked sieving membrane holes, or unblocking holes which may have become blocked by particles. When coupled with an air valve and source of dry air, the wiper may assist in providing a zero humidity environment within the sieve stack to reduce particle agglomeration and ease sieving for smaller (<20 microns) particles at relevant mesh sizes by distributing the dry air throughout the particles while agitating them to permit the air to permeate through the mass of material being sieved. The use of the wiper may simplify design and mechanical considerations for the sieving stack, and simplify maintenance functions such as assembly, operation, and cleaning.

The wiper may be operated so as to provide automated wiper control, including speed, duration, and direction control. The wiper assembly provided in accordance with the invention incorporates wiper blade materials that avoid damage to the sieving membrane/mesh.

When a sieving technique is used for particle deposition in accordance with the invention, it is an aim of the invention to speed up the particle deposition process when sieving by employing a continuous blade, a segmented blade, or a brush that contacts the surface of the sieving membrane or the layer of particles provided thereon, improving sieving uniformity by increasing contact between the particles and the sieve, and reducing clogging of pores in the sieve. The blade, segmented blade, or brush in accordance with the invention may refer to structures that are formed of any materials that do not react with or damage the sieve or the particles of material being sieved. These materials include, but are not limited to, rubber or silicone blades, and natural or synthetic bristles.

Figure 9A:
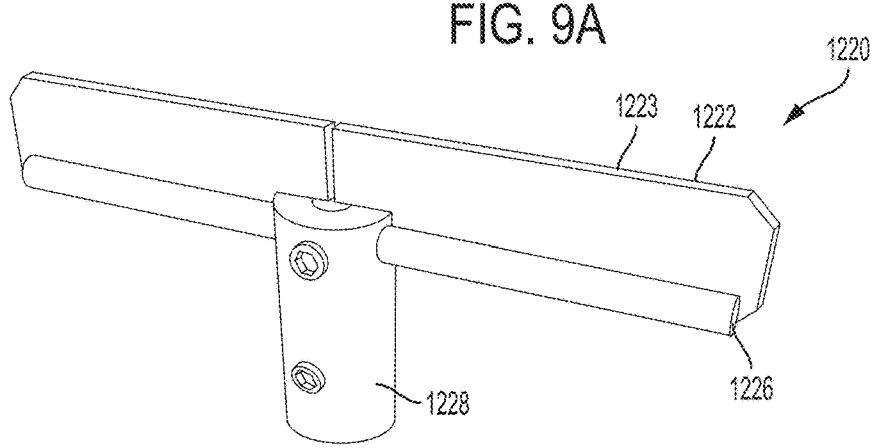
FIGS. 9A-9C are drawings of various embodiments of the wiper.
Figure 9B:
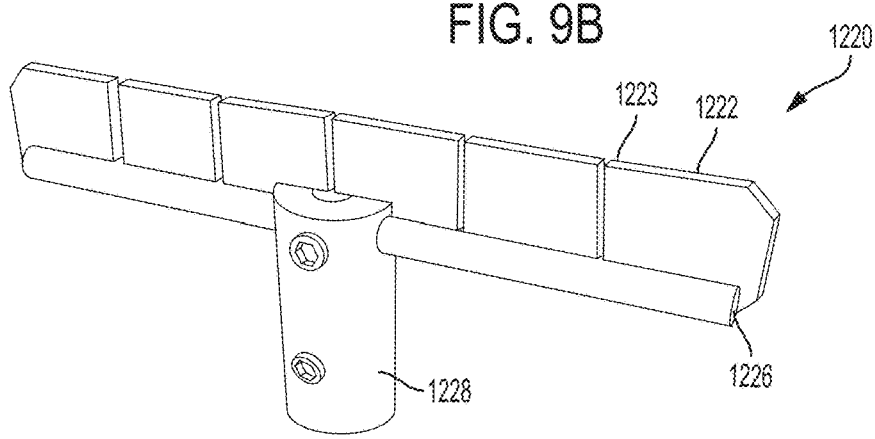
Figure 9C:
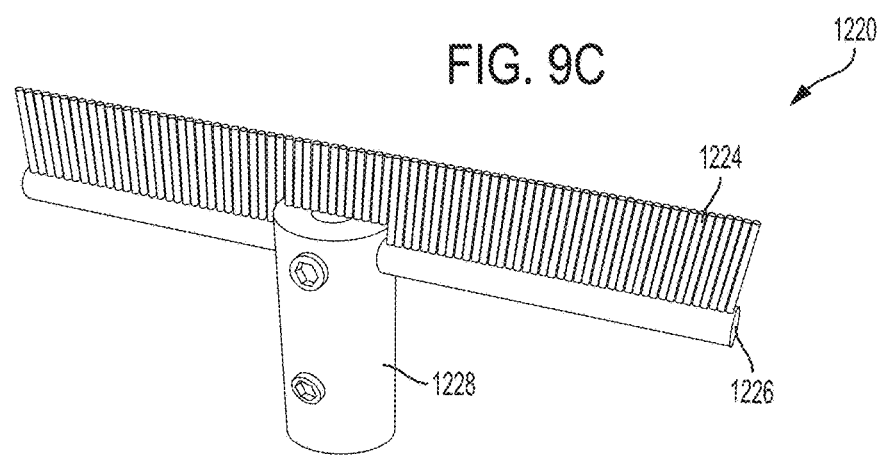

Examples of blade configurations are shown in FIGS. 9A-9C. In FIG. 9A, a rotating wiper 1220 is shown with the blade portion 1222 affixed to a blade housing or arm 1226, which is in turn affixed to a spindle or rod 1228 that is adapted to be rotated (for example, by stepper motor 1500, shown in FIGS. 2B and 3). FIG. 9B shows a rotating wiper 1220 in which blade 1222 incorporates several segments, notches, or gaps 1221 therein, to impart additional flexibility to the blade as it passes over the particulate material and sieve screen. FIG. 9C depicts an aspect in which the blade is replaced with a brush 1224. Preferably, the blade, segmented blade, arm, or brush rotates over the surface of sieve, and therefore is provided on a rod 1228 that is affixed to a motor or other means for rotating, where the rotation speed may be controlled by a user, or by a processor that determines the rotation speed based on user input parameters or based on feedback regarding particle flux, rates of particle throughput, and/or particle loading on the coupons.

The wiper blade construct in accordance with this aspect of the invention was fabricated in two main pieces, including a wiper base support 1226, 1228 assembled onto a stepper motor shaft (not shown), and interchangeable blades, segmented blades, or brushes that are attached to the wiper base. The interchangeable blades may be fabricated from a rubber material. The design positions the edge of the blade in intimate contact with the sieving membrane/mesh. The blade material should be selected to be soft enough to avoid damaging the sieve, but also stiff enough to push the particles across the surface of the sieve. One purpose of the wiper is to spread the particulate material around the sieving membrane/mesh to avoid particulates pooling in one area. The wiper may also accelerate or force particulates through the openings of the sieve. In FIG. 9A, the blade can be seen to actually consist of two separate pieces 1222, which may be formed of rubber, although a one piece blade is also envisioned in accordance with the invention. The optional blade separation is beneficial because it allows different blade pieces to flex and bend in opposite directions while rotating or switching directions.

To improve the sieving mechanism and maintain blade contact with the sieving membrane surface, a blade having a thin or sharp edge 1223 is preferred, as shown, for example, in FIG. 9A. The blade preferably retains sufficient rigidity to spread the particles across the sieve surface and force them through the sieve membrane. Its design retains sufficient flexibility to allow it to adapt to the surface morphology of the sieving membrane. This ensures that all the particulate material in the sieving pan is continuously moved during sieving, and avoids particle pooling.

The lid of the sieving pan can be modified so that a motor is positioned on top of it. In this aspect of the invention, the shaft of the motor reaches through the lid into the sieving pan and the wiper blade is attached to the end of the shaft. The lid may also be modified to attach a dry air supply (see FIG. 3A, 1600). The connection between the wiper and the shaft of the stepper motor is height-adjustable, and allows for blade-sieving membrane clearance optimization. A transparent sieving pan lid 1100 may optionally be provided to permit direct viewing of the 1200 sieve pan to assess whether wiper blade adjustment is required. The transparent lid is preferably formed from a plastic material, though a glass lid is also envisioned.

The rotation of the wiper may be generated, for example, by using a windable spring-based mechanism, or a motor. The motor is preferably a stepper motor, having a housing that is preferably rigid, and can be clamped to the sieve stack assembly 1000, as shown in FIGS. 3A and 3B, 1500. It will typically not be necessary to build an extra housing to protect the motor from clamping forces or impact hammer tapping, though such additional features are within the scope of the sieving apparatus of the invention.

The lid with the stepper motor, wiper/blade/brush, and dry air supply is shown in FIG. 3A. The wiper mechanism 1220 is shown installed on top of a sieving pan 1200, which itself is mated to a collection pan 1300 with the coupon holder 1400 positioned inside it. The attached stepper motor controller is provided on top of lid 1100. The controller 1700 can also optionally control the rotation of the rotating coupon holder 1430, when provided.

A microcontroller may be used to control the motor and blade/brush. One exemplary microcontroller that may be used in accordance with the invention is the Arduino® microcontroller from Adafruit Industries, New York, N.Y., though the invention is not limited to any particular microcontrollers or associated software. In-house developed firmware allowed for control of various blade or brush functions including: rotation speed, rotation time duration, rotation direction, continuous or alternating direction motions, and timing synchronization with the Gilson Performer® III3 sieve shaker unit. Additionally, the microcontroller is able to control rotations in certain patterns, for example, by switching the rotation direction after every 2 full rotations of the wiper. Rotation direction may also be adjusted based on time, sensed particle deposition, or other factors input by a sensor or other device. It will be appreciated that a general purpose controller may be used, and that the controller may optionally be programmed to carry out these or other blade or brush functions.

In some aspects of the invention, the stepper motor controller is separate from the controller for the sieving stack shaker, but it is envisioned that the same controller can be used to control all sieving apparatus functions. The use of a single controller may beneficially allow synchronization of operations.

The complete sieving stack assembly is compact and easy to handle. The individual parts are simple to assemble and disassemble. Minor or no adjustments are required to position the blade after an initial adjustment is made to establish its contact with the sieving membrane surface.

As a result of these sieving operation design improvements achieved by the apparatus and methods of the invention, the following improvements can be realized: dramatically (>10×) decreased sieving time duration to achieve a target areal loading; and significantly improved uniformity of deposited particles over the coupons contained in the collection pan, and across the width of the collection pan. The time saving is believed to be primarily due to the wiper blade action which drives particles through the sieving membrane or mesh. The wiper blade spreads particles in the sieve pan across the sieve membrane and distributes them in a more uniform (average) fashion across the sieving membrane surface. The uniformity of the deposited particles is a direct function of this enhancement.

As a general comment regarding the sieving membrane design used in conjunction with a wiper assembly, a non-woven flat mesh or membrane design is preferred. For a sieving membrane fabricated with a woven wire design, the membrane is inherently an uneven surface. In this case, because the blade only swipes over the higher points of the mesh, this increases the possibility of particles blocking holes. A brush design may help in this regard. Fibers with a diameter comparable with the mesh opening sizes maybe particularly useful in clearing any blockages. Even if the sieving mesh or membrane is flat, it still may be difficult to ensure contiguous contact of the blade with the sieving membrane so a brush assembly may be generally preferred over a solid blade, particularly for deposition of particulates that are more prone to aggregating and forming sieve blockages. A segmented rubber blade is also envisioned as a possible solution to maintaining good contact between the blade and the sieving membrane.

In an additional aspect of the invention, the clogging of the sieve mesh may further be prevented by incorporating a series of ultrasonic actuators ringed around the exterior edge of the sieve pan and in line with the sieving membrane (not shown). The actuators may be used in place of a wiper assembly, or in addition to a wiper assembly. Upon activation, the actuators may be used to dislodge the clogged particles.

Feedback Control.

Another improvement described here are different feedback control mechanisms to allow the sieving process to be automatically halted when a target loading has been reached. The sieving process is influenced by considerations including, but not limited to, the preprocessing of particulate material (manual or automated pre-grinding), the sieving membrane structure (woven or non-woven mesh) and the blade or brush design.

In some embodiments, a window may be provided in collection pan 1300 to view the deposited particles, extension sleeve 1310 may be formed using a transparent material, or a quartz crystal microbalance may be provided adjacent to the coupons in order to monitor particle deposition and provide feedback control for the deposition procedure. When provided, the window or windows may preferably be formed in the bottom of the pan to provide a direct view of at least one coupon. One or more windows provided in the side of the pan are also envisioned. An optical in situ measurement or in situ miniature resonating device such as a quartz crystal microbalance (QCM) or related surface acoustic wave (SAW) sensor could provide the capability to halt the deposition process when a desired particle loading has been achieved on one or more of the coupons. Because there is normally more than one coupon being coated, one or more coupons can serve as a witness coupon which is continuously monitored. This aspect of the invention can be particularly useful when the witness coupon is a glass microscope slide and the other coupons are substrates which are too rough to be considered for visible microscopy characterization. Another approach could include a miniaturized digital camera unit with corresponding optics (for example, a magnifying lens system) embedded into the coupon holder base to allow direct monitoring of particles deposited by looking through a glass coupon during the particle loading progress. Regardless of the mechanism used to detect the particle loading, the deposition process may be halted, for example, by stopping the sieving of the particles (e.g., by turning off the wiper mechanism or vibration generator), or by deploying a mask to prevent deposition of further particles on the coupons after a desired loading has been reached.

By incorporating one or more of a rotating coupon platform below the sieve in the collection pan, a wiper-assisted sieving procedure, and a window or resonating device to observe depositions or provide feedback control in real time, the sieving apparatus and methods of the invention beneficially provide faster and more uniform deposition of particles of interest onto one or more coupons or test substrates.

Dust Storm

Figure 10:
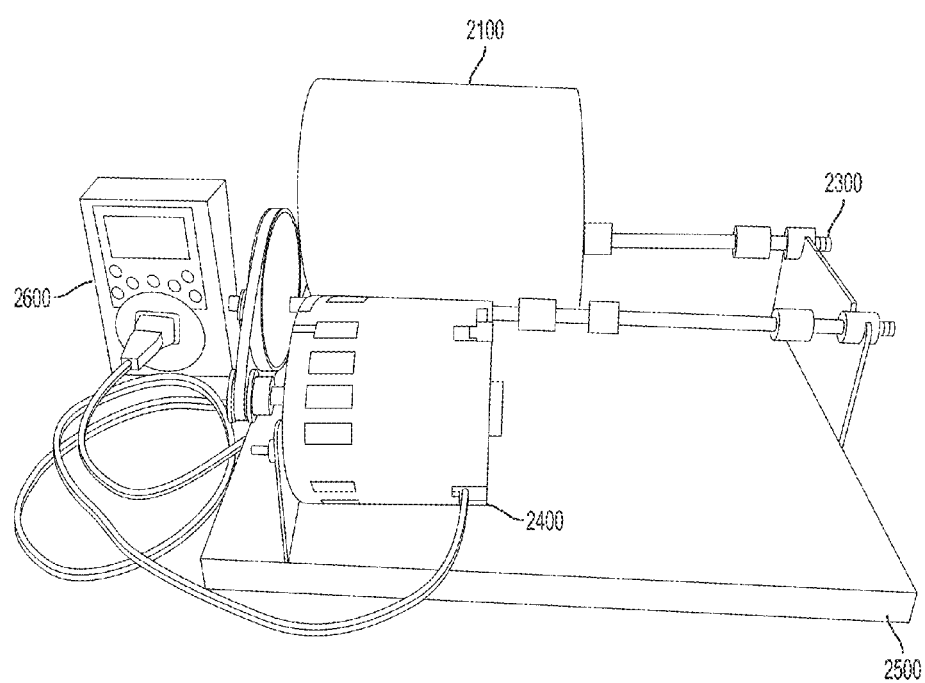
FIG. 10 is a drawing of a ball-milling apparatus and controller, with a ball-milling container provided thereon.
Figure 11:
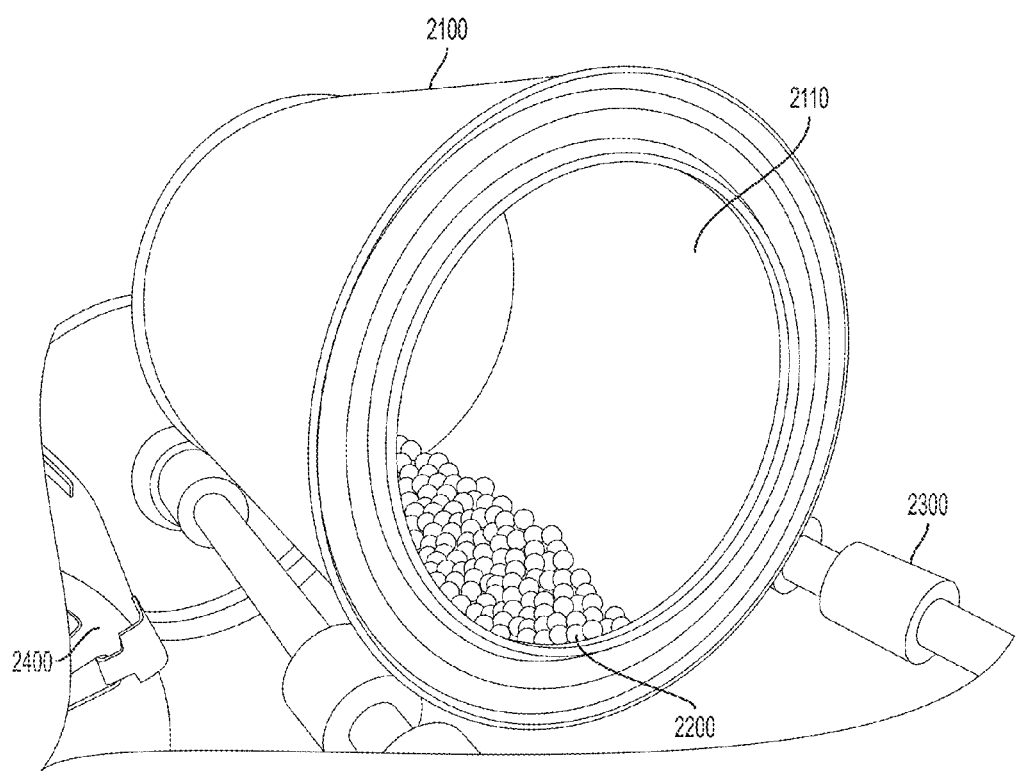
FIG. 11 is a drawing of ball-milling container provided on the rollers of a ball-milling apparatus, showing the balls contained inside the opening of the container.

In other embodiments of the invention, the particles to be analyzed are deposited by a dust storm apparatus and method as shown in FIGS. 10-11. The dust storm apparatus may incorporate a blower assembly, a fan assembly, or an acoustic transformer in order to create a particle cloud. It is understood that the speed at which the blower or fan is operated, or the frequency at which the acoustic transformer is operated, may be selected in order to cause particles of a certain weight and/or size to be dispersed within the atmosphere found in the container. Other particles present in the container housing the blower, fan assembly, or acoustic transformer that are larger or heavier are not dispersed into the atmosphere of the container. In still other embodiments of the invention, the particles to be analyzed may be sieved before being deposited by the dust storm technique. Alternatively, the particles to be analyzed may be ground using a mortar and pestle (automated or not), or milled (for example, using a ball mill) before being deposited by the dust storm technique. Such pre-deposition or pre-fractionation processing may beneficially improve the consistency of the particles deposited using the dust storm.

The dust storm deposition apparatus and methods of the invention permit faster deposition of particles of interest in a controlled fashion to provide a uniform distribution of a known or targeted amount of the particles on one or more coupons or substrates. The invention provides real-time feedback control over the particle deposition process, including the ability to halt deposition when a target loading has been achieved. This has not been possible using existing sieving or inkjetting technology.

Dust storm deposition offers a rapid approach for loading a targeted amount of particles on a substrate. Uniform particle coverage is possible under controlled conditions. However, a relatively large particle that will not stick on the coupon surface can knock off a cluster of smaller particles to leave a bare patch of coupon. Prefractionation of the particulate material can eliminate undesirable large particles which are the source of this effect. For a glass coupon substrate, in situ monitoring using a visible camera provides a path to provide feedback control and turn off the dust storm when a targeted loading has been achieved. Alternately, a gravimetric device such as a quartz crystal microbalance (QCM) may be used to indirectly detect the weight of deposited particles on a coupon.

Figure 12:
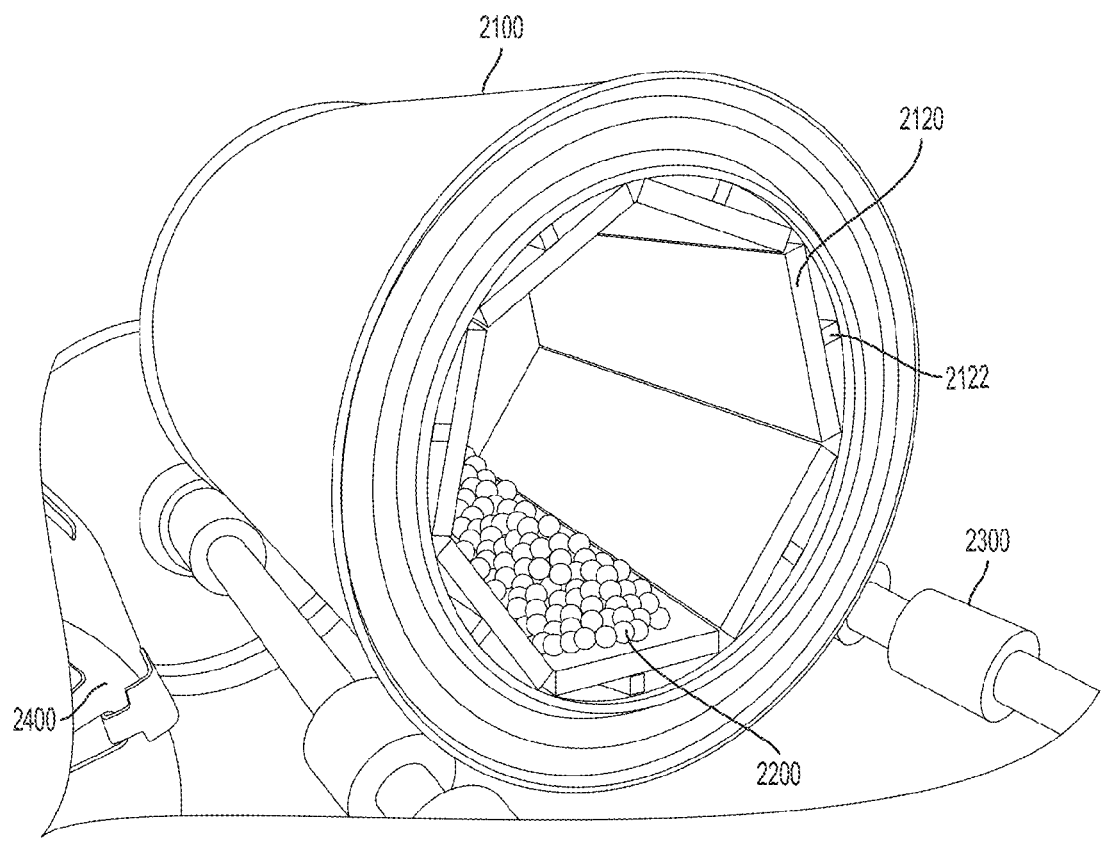
FIG. 12 is a drawing of an alternative ball-milling container having strips removably mounted to the inner walls of the container.
Figure 13:
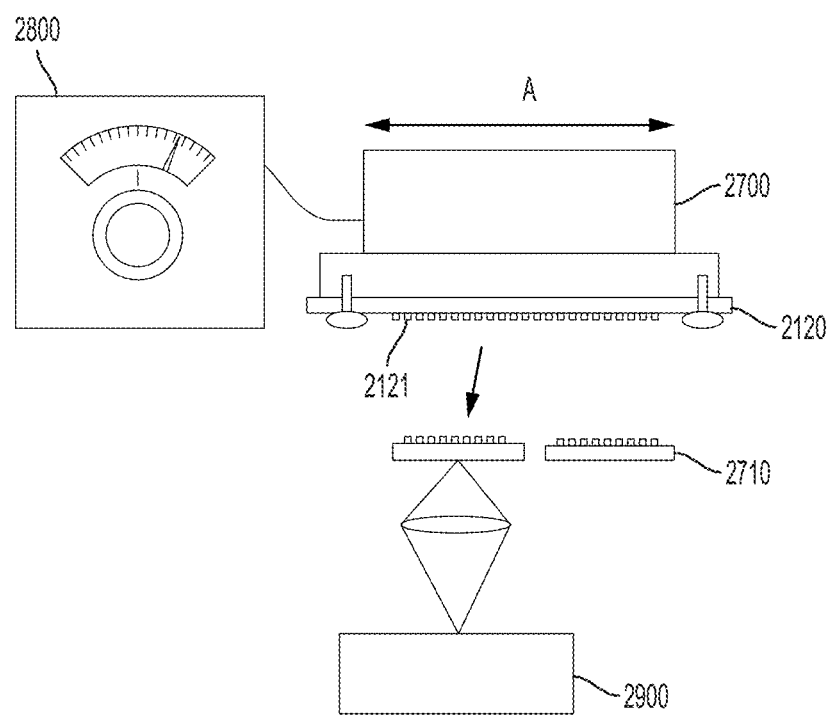
FIG. 13 is a drawing of an ultrasonic dust storm assembly for creating a dust storm using particle-coated strips.
Figure 14A:
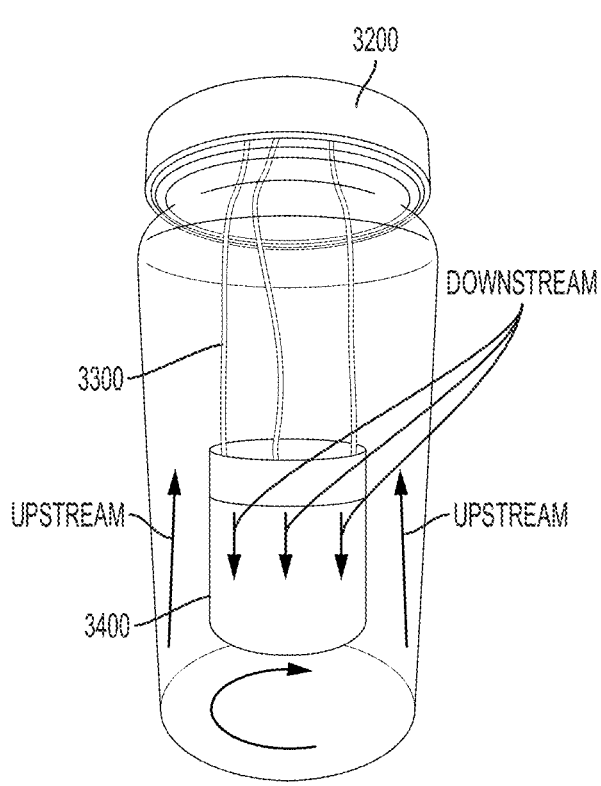
FIGS. 14A-14C are drawings of a dust storm apparatus.
Figure 14B:
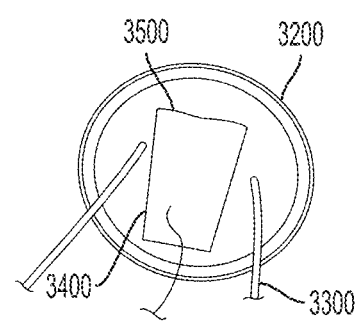
Figure 14C:
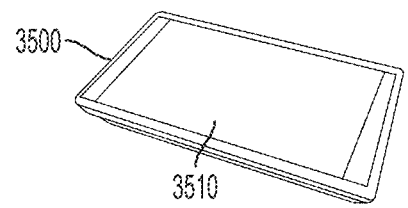
Figure 15:
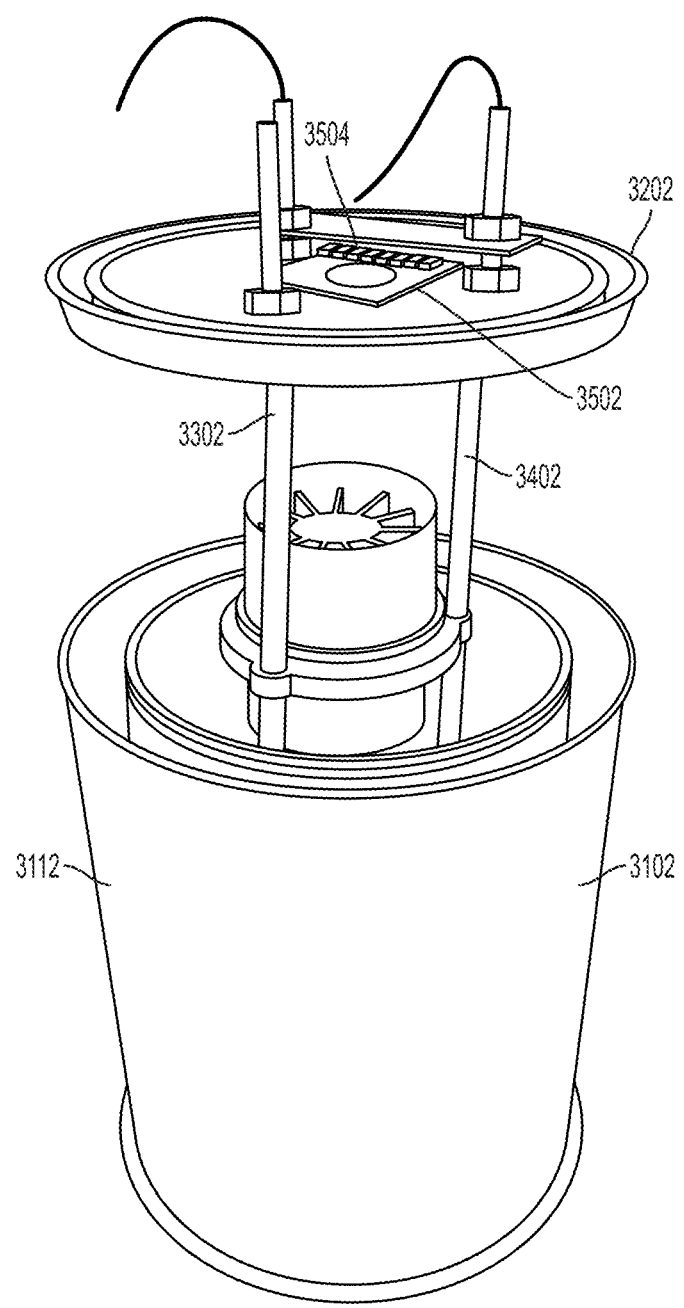
FIG. 15 is a drawing of an alternative dust storm apparatus in which a lid adapted to fit the opening of a ball-milling container includes a coupon mounting portion and a blower attached thereto. The coupon is provided on the outside of the lid for the container, and is masked by an opening in the lid.
Figure 16:
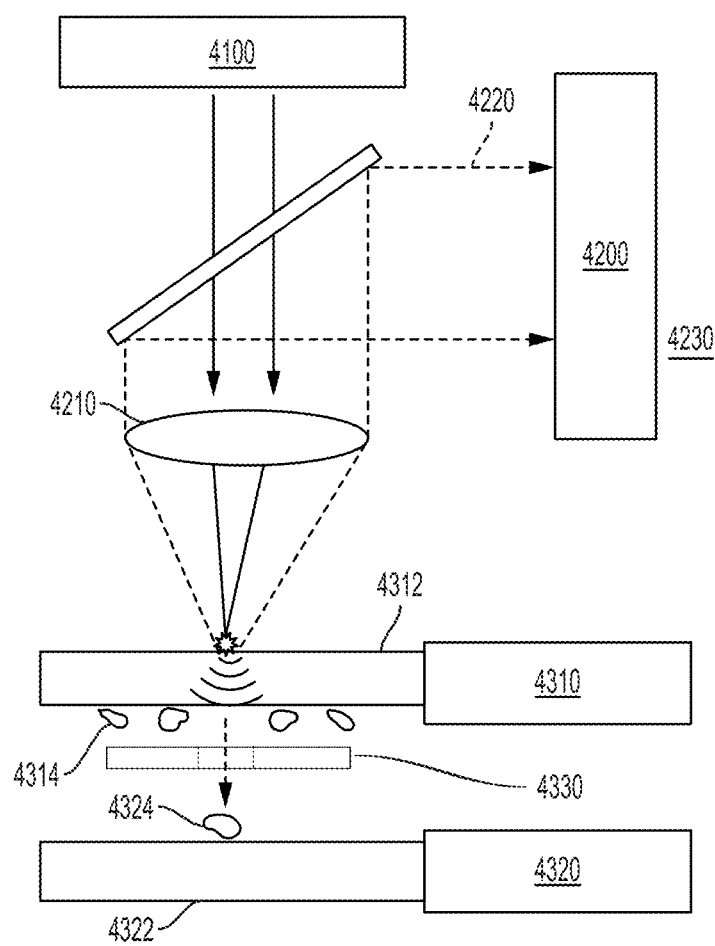
FIG. 16 is a drawing of a laser particle printing apparatus including motorized stages for holding a receiving substrate and a particle-coated source coupon.

Exemplary particle milling apparatus are shown in FIGS. 10-12. Dust storm apparatus used to achieve particle distribution on a coupon in accordance with the invention are illustrated in FIGS. 13-15.

Particle Pre-Processing.

According to one aspect of the invention, the particles to be deposited using the dust storm method and apparatus may optionally be pre-processed to more closely target the size distribution of the particles for a particular application, and eliminate larger or smaller undesirable particles such that the desired particle size range is more closely achieved prior to initiating the dust storm. When the terms "uniform distribution" and "substantially uniform distribution" are used in accordance with the various embodiments of the invention, it is understood that for areal densities of particles ranging from 0.01 to 200 micrograms/cm$^2$ provided on the coupon or substrate in the desired areas as a result of using the apparatus and methods of the invention the areal density on average varies by less than 100% in the target region coated. Preferably, the particle areal density varies by less than 50% in the target region coated. More preferably, the particle loading areal density varies by less than 10% in the target region coated. Most preferably, the particle loading areal density varies by less than 3% in the target region coated. In some aspects, the particles are milled until substantially all are within about +/−10% of the target particle size range extremities. It is understood that the desired target particle sizes, range of particle sizes, and the amount of particles within a set of milled particles that meet the target or fall within a desired range may depend on a number of considerations. These considerations may vary, for example, depending on the particle being deposited using the dust storm technique, and the nature of the further analysis to be conducted using the particles.

The pretreatment of particles prior to applying the dust storm technique(s) may be based on commercially-available milling apparatus due to the more uniform particles produced, although manual techniques such as grinding of particles with a pestle and mortar may also be used for particle pre-processing in accordance with the invention. Milling apparatus suitable for use in the invention include apparatus suited for dry milling to produce fine particles, and may include ball mills, rotor mills, mixer mills, planetary ball mills, jet mills, impact mills, mortar grinders, and jar mills. In some embodiments of the invention, a standard commercially-available ball mill machine can be used, and optionally upgraded with a programmable power plug to time the milling and a dry atmosphere to perform the milling under. One example of a ball mill apparatus can be seen in FIG. 10, and includes a motor 2400 provided on a base 2500 that is controlled using controller 2600. Motor 2400 actuates a rolling component 2300 configured to rotate a canister 2100 horizontally about its long axis.

Ball milling is a preferred technique in accordance with one aspect of the invention. Another view of an exemplary ball milling apparatus is shown in FIG. 11. The canister 2100 used for the ball milling may incorporate metal sidewalls 2110, and be adapted to receive a lid (not shown). Steel ball bearings may be used as milling balls 2200, but balls formed using other materials such as ceramic or rubber are also suitable. (In the case where explosive materials are being milled the use of rubber balls or rubber coated balls may be preferred.) The amount of ball bearings may vary depending on the composition being milled. The use of too few bearings may result in pushing the material just ahead of the line of bearings, resulting in minimal milling. In one preferred aspect, the amount of balls loaded into the canister was sufficient to cover the entire floor or bottom of the can. The amount of ball bearings used should be large enough to force the balls to tumble over each other in order to produce the desired milling. The tumbling and the total mass/weight of the milling balls enabled raw material grinding to particles of the desired particle sizes.

The choice of material selected for the canister and milling balls varies, and the selection of these and other ball milling conditions are within the skill of those skilled in the art. For example, when both the canister and ball bearings are made of steel, the texture present on the inner surface of the canister and the balls (particularly if combined with moisture in the air within the canister used for the ball milling apparatus), can result in most of the ground material sticking to the inner surface of the canister and the surfaces of the balls. However, even if most material is adhered to the ball milling apparatus, small loose particles will also be present that can be used for later deposition on a coupon substrate using the dust storm approach. This observation leads to the recommendation that very smooth milling canisters and ball bearings may be preferred in order to reduce particle adhesion, or that a large amount of raw material be provided, or a combination of both, in order to optimize the efficiency of the ball milling step when used in accordance with the invention.

A variation of the ball milling container is shown in FIG. 12, in which container 2100 is lined with metal strips 2120 that are attached to the inner wall 2110 of the container by clamps, suction cups, or other attachment points 2122. As the ball grinding proceeds, particles are deposited onto these strips. Afterwards, the container is disassembled, and particle-coated individual strips 2120 may be removed.

Milling can beneficially provide a more predictable range of particle sizes than a manually-operated mortar and pestle, or the use of the bulk composition prior to processing. If the variables including time duration, can size, ball size, ball weight, number of balls, and the amount of raw material are controlled, the ball milling technique in particular can be used to produce a predicable particle size range and amount.

Dust Storm Apparatus and Methods.

In one aspect of the invention, the particles to be deposited on the coupons are deposited using a dust storm. The dust storm technique beneficially results in a random distribution of particles on the surface of a test coupon. A dust storm effect may be created using a variety of apparatus capable of causing particles to be dispersed into the atmosphere in a manner such that they can be deposited onto one or more test coupons. Non-limiting examples of apparatus that may be used to generate a dust storm of particles include ultrasonic actuators and fans.

The dust storm apparatus and method incorporating an acoustic transformer may be operated at a frequency capable of generating a cloud of particles from a surface having particles deposited thereon. The frequency at which the acoustic transformer is operated may be adjusted in order to cause particles of a certain weight and/or size to be dispersed from the particle-bearing surface into an atmosphere. In some aspects, an acoustic transformer may be used to ultrasonically agitate an entire ball-milling container after particles have been milled therein, causing particles deposited on the inner wall of the container to be released.

The acoustic transformer allows for controlled release of particles from a substrate (e.g., a ball-milling container, a coupon, etc.) by adjusting the intensity or frequency of the ultrasonic waves. This technique provides a distinct advantage in that it allows for preferential deposition of a desired particle size by adjusting the ultrasonic frequency. Without wishing to be bound by theory, it is believed that this is due to the fact that the adhesion force between a particle and a substrate is proportional to the contact area of the particle. At low ultrasonic intensity, only the large particles fall off of the substrate. As the intensity of the ultrasonic waves is increased, smaller and smaller particles begin to detach from the substrate.

In accordance with a method for ultrasonic particle deposition, particles larger than a desired size are removed first (whether ultrasonically or by other means), after which a sample coupon may be placed under the substrate to collect the particle size or sizes of interest. Another advantage is that the sample coupon is free from contact with the particle source (unlike, for example, in a sieving stack where the sample coupon is enclosed inside the collection pan.) This allows more complex sample or coupon holders, including those with planetary motions (for particle deposition uniformity), as well as the possibility for in situ monitoring of the particle deposition process. For example, it would be possible to position the ultrasonic deposition apparatus and substrate above an inverted microscope positioned so as to view a glass witness coupon with the actual sample coupon next to it while the deposition container moves back and forth over the two coupons.

As shown in FIG. 13, a strip coated with particulate matter may be inserted into an ultrasonic apparatus 2700 that may be controlled using controller 2800. When a particle-coated strip 2120 is placed on the ultrasonic apparatus 2700 and subjected to ultrasonic vibrations, particles 2121 are dislodged from the surface of the metal strip 2120 and fall onto one or more test coupons or substrates 2710. The loading of particles 2121 on the substrates 2710 may be controlled in some aspects by viewing the particle loading with an optical instrument 2900, such as a microscope. In this configuration, the ultrasonic source 2700, particle-coated strip 2120, and the coupons 2710 can beneficially be used without having to be provided within a container.

The fan-based dust storm apparatus and methods of the invention are depicted in FIGS. 14 and 15.

As shown in FIG. 14, a fan apparatus 3400 is provided in a separate container 3100 and suspended from container lid 3200 using wires 3300. When actuated, fan 3400 creates a dust storm by moving air in the directions indicated by arrows in FIG. 14. Particles that have been ground using a ball mill or other grinding apparatus may be placed in the dust storm apparatus for deposition onto one or more test coupons 3510 housed in a coupon holder 3500, which may be positioned in the lid 3200, or along the sides or bottom of the container 3100 (not shown). In some embodiments, the container used for the grinding or milling may be directly affixed to the lid 3200 having the dust storm assembly attached thereto. Unprocessed particulate matter may also be used in the dust storm apparatus, and the fan speed selected such that only smaller particles will be dispersed into the atmosphere of the container for deposition on test coupons.

In accordance with another aspect of the invention shown in FIG. 15, a dust storm apparatus may be adapted for use directly with a ball mill container which has been used to grind particles. The ball mill container may be adapted to accept a fan-based blower system 3402 and suspended from a ball mill container lid 3202 by suspension arms 3302. A coupon platform 3502 may be positioned within the container, for example, by affixing it to the wall 3112 of container 3102. The coupon platform 3502 may also be attached to the upper or lower surface of lid 3202. In certain preferred aspects, the coupon platform is attached to the upper surface of the lid 3202 and an aperture is provided in lid 3202 (not shown) to serve as a mask, thereby allowing the particles within the container to be blown around in a random fashion and deposited on one or more coupons secured to the lid of the container.

The fan-based dust storm apparatus described above may be implemented in order to avoid the need to transfer particulate matter from the milling container into a separate dust storm apparatus. The fan/blower is placed within the container by attaching the lid, preferably the coupon platform is provided opposite to the fan. The fan may be provided at the bottom of a container and the coupon platform may be provided on the lid of the container. Alternatively, the fan may be affixed to the lid of the container, and the coupon platform may be provided at the bottom of the container. The fan may be suspended within the container, and the coupon platform may be provided at the top or bottom of the container. In other aspects, the fan may be provided on the bottom of the container or on the lid of the container, and coupons may be affixed to the walls of the container.

In some dust storm apparatus, the action of the fan may beneficially establish cyclonic airflow within the container, causing the particles to rotate around the inside of the container and be dispersed within the atmosphere of the container while continuing to rotate.

In order to break up possible agglomerations of particles being subjected to dust storm processing, lightweight beads may be included in the container along with the particles. For example, polymer or plastic beads may be used. Polyethylene (PE) beads are preferred in some aspects of the invention, but any beads that are lightweight enough to flow with the particles may be used, and beneficially permit visualization of the air flow patterns established by the blower fan.

A microcontroller may be used to control either the blower fan or acoustic transformer. One exemplary microcontroller that may be used in accordance with the invention is the Arduino® microcontroller from Adafruit Industries, New York, N.Y., though the invention is not limited to any particular microcontrollers or associated software. In-house developed firmware allowed for control of various fan or transformer functions, including: blower speed, fan blade rotation direction, continuous or alternating fan rotation direction, ultrasonic wave intensity, and synchronization with a rotating coupon platform. It will be appreciated that a general purpose controller may be used, and that the controller may be programmed to carry out these or other functions.

Coupon Platform.

One or more test coupons used in accordance with the invention may be held in a stationary position in order to allow particles from the dust storm apparatus to be deposited thereon. In other aspects, the one or more test coupons may be held on a moving platform in order to compensate for any lack of uniformity in depositing particles during the dust storm process. The moving platform may be a rotating platform, and more preferably, the rotation speed of the moving platform may be controlled using a processor. The processor may be programmed to permit a user to vary the rotation speed. Alternatively, the processor may be programmed so that the rotation speed is adjusted automatically based on information regarding the particles (such as density and size), the airflow speed and direction within the apparatus, the detection of particle flux non-uniformities, and the loading level of the coupon or coupons, beneficially permitting end result-controlled test coupon fabrication that achieves specific desired particle size and areal coverage parameters.

Feedback Control.

Another aspect of the invention includes different feedback control mechanisms to allow the dust storm process to be automatically halted when a target loading has been reached. An optical in situ measurement or in situ miniature resonating device such as a quartz crystal microbalance (QCM) or related surface acoustic wave (SAW) sensor may provide the capability to halt the deposition process when a desired particle loading has been achieved on one or more of the coupons. Because there is normally more than one coupon being coated, one coupon can serve as a witness coupon that is continuously monitored. This aspect of the invention can be particularly useful when the witness coupon is a glass microscope slide and the other coupons are substrates which are too rough or provide too poor particle viewing capability to be considered for visible microscopy characterization. When provided, a window or windows may preferably be formed in the lid or container housing the coupons, in order to provide a view of at least one coupon. Another approach could include a miniaturized digital camera unit with corresponding optics (for example, a magnifying lens system) embedded into the coupon holder base to allow direct monitoring of particles deposited by looking through a glass coupon during the particle loading progress.

Regardless of the mechanism used to detect the particle loading, the dust storm process may be halted, for example, by stopping the blowing of the particles or ultrasonic wave transmission (e.g., by turning off the fan/blower or acoustic transformer), or by deploying a mask to prevent deposition of further particles on the coupons after a desired loading has been reached.

Laser-Assisted Deposition of Selected Particles

Coupons having particles of interest deposited thereon may be beneficially used in further apparatus and methods. In one preferred embodiment of the invention shown in FIG. 16, the particles 4314 deposited on a coupon 4312 may be individually visualized by acquiring an image of a loaded coupon (for example, using a high resolution camera or microscope 4200 with a 20× reflecting objective 4210 that reflects the image off of mirror 4220), displaying the image on a display or printed image 4230, and cataloguing the position and size of each particle using existing image processing techniques. Once the particles have been catalogued, specific particles of interest 4324 may be individually identified for further processing.

In one aspect, individual particles of interest (identified based on their shape, size, composition, or other considerations) may be removed from the coupon 4312 by utilizing a pulse from a laser 4100 to generate a mini shock wave in the coupon in the area where the individual particle being removed is located. Lasers suitable for use in the LSD technique include gas lasers (e.g., $CO_2$ lasers), solid-state lasers (e.g., YAG lasers), and any other laser suitable for use in dislodging particles of interest from a coupon without altering the particles of interest or the particles in the areas surrounding them. In some aspects of the invention, pulsed $CO_2$ lasers are preferred. The energy of the $CO_2$ laser is absorbed by the top surface of the loaded glass coupon (i.e., the side not coated with particles), so no laser damage occurs to the particles or the optional glass optics that may be used to guide the stages. In some aspects of the invention, more than one laser may be provided to increase throughput.

The shock from the activation of the laser causes the particle of interest 4324 to fall off of the coupon 4312 and onto a second coupon or other substrate 4322. A mask 4330 may optionally be provided to prevent unintended deposition of particles on the second coupon, for example, if the laser dislodges a neighboring particle at the same time that the particle of interest is dislodged, or if the particle of interest deviates from its expected path when falling from the first coupon. Receiving substrates prepared in this manner may beneficially be used for calibration or testing of standoff detection apparatus.

The technique is agnostic towards the receiving substrate, and exemplary materials for use as receiving substrates include glasses used in consumer electronics or automobile applications; silicate glasses, such as soda lime glass and borosilicate glass; metals; painted metals; wood; paper; cardboard; and woven cloth of all material types and woven configuration. A wide range of polymers may also be used as receiving substrates in accordance with the invention, such as polymethylmethacrylate, polystyrene, Bakelite, polyvinylchloride, nylon, polyethylene terephthalate, polyurethane, polycarbonate, or polyethylene. The loaded coupon having particles of interest thereon may be formed using any material, and are preferably formed using materials that minimizes the area over which the shock wave caused by the laser beam is transmitted. This reduces the likelihood that a particle located near the particle of interest will be dislodged from the loaded coupon along with the particle of interest. This may be accomplished by using a material that exhibits poor shock wave transmission, reducing the thickness of the coupon, or both.

The accuracy of particle deposition onto a receiving substrate when using the LSD technique may be improved by placing the first and second coupons 4312 and 4322 on moveable stages 4310 and 4320, so that the falling particle 4324 lands at a designated coordinate on the receiving substrate 4322. The position of the first stage 4310 may be adjusted so that the particle of interest 4324 is in the center of the field, where the laser is focused. Then the second stage 4320 with the receiving substrate 4322 is moved into position so that the particle of interest 4324 free-falls directly down onto a desired location. The distance between the loaded glass coupon and the target substrate is preferably minimized so that no significant X-Y deviation occurs during particle free-fall. The atmosphere surrounding the first and second stages 4310 and 4320 may be controlled to prevent air currents or temperature gradients from influencing the particle of interest as it falls from the loaded coupon to the receiving substrate, and in some aspects, this control may include applying an electric field to the coupon and receiving substrate to minimize deviations during particle free-fall. In some aspects of the invention, the stages may be part of the optical visualization apparatus 4200, such as a microscope, which may be used to identify particles of interest. Additionally a mask may be used (not shown) between loaded coupon 4312 and receiving substrate 4322 to ensure only the intended particle 4324 has line of site to the receiving substrate 4322 and other particles 4314 cannot land on receiving substrate 4322 if one or more also happen to become dislodged from the loaded coupon. In those aspects of the invention where multiple lasers are used, multiple sets of first and second stages and/or rotating sets of first and second stages may be used to deposit particles on multiple receiving substrates.

In order to print a pattern using the particles 4314 provided on substrate 4312, there is no limit to the number of times that the laser may be activated in order to remove a particle of interest 4324 from the substrate 4312 to cause it to be deposited on a desired location of target 4322. While printing the target 4322, if particles of a certain desired type become exhausted in the image of the loaded glass coupon 4312, the invention beneficially permits the printer to move the first stage to a different part of the glass coupon, or load a new stock coupon into the first stage and repeat the image analysis, in order to continue printing particles on the same target coupon loaded into the second stage. Any number of particles may be deposited in any desired pattern using this aspect of the invention.

This Laser Shock Deposition (LSD) technique can also be used to remove individual particles that are not of interest from a coupon. The particles selected for removal may have a shape, size, composition, or other feature that is not desired, leaving only the particles of interest on the coupon.

The receiving substrate may optionally be pre-treated to have a composition present on its surface, such as a layer or pattern of background material that may be present in an environment where the particle of interest is to be detected. For example, a pattern mimicking a fingerprint may be deposited using sebum, sweat, or sebum/sweat derived compounds on the receiving substrate, and one or more particles of interest may be knocked off of the coupon and onto a specific location on the receiving substrate. The coupons prepared in this manner may beneficially be used for calibration of standoff detection apparatus. It is also envisioned that a layer of fabric, lint, hair, or other material could be provided on substrate 4322 to mimic an environment where particle 4324 is to be detected.

The LSD system of the invention may be used in accordance with a method for custom printing substrates with particles of interest. The patterns in which the particles may be deposited are unlimited, and can be adjusted to suit the use for which the substrate is being prepared. For example, in order to test standoff detection equipment, patterns mimicking fingerprints, footprints, smudges, smears, or other effects may be used. In some aspects, the particles may be printed in a uniform pattern, such as a grid. The particles may be loaded in graduated amounts to produce a set of calibration standards, which may be used to quantify the amount of a particular particle present in an unknown sample, or to aid in determining lower limits of detection for a particular standoff detection apparatus.

The coupons prepared using the LSD apparatus and method described herein may beneficially be used for calibration or testing of standoff detection apparatus, which may be used in determining the presence or absence of particulate materials found in explosives, chemical or biological weapons, narcotics, or environmental pollutants. They may also be used for evaluating pharmaceuticals, cosmetics, cement materials, ink components, food substances (including, without limitation, sugar and flour), contaminants of any of these materials, and any other compositions that are supplied or may be detected in powder or particulate form. Additional applications are envisioned within the scope of the invention.

EXAMPLES

The invention will now be particularly described by way of example. However, it will be apparent to one skilled in the art that the specific details are not required in order to practice the invention. The following descriptions of specific embodiments of the present invention are presented for purposes of illustration and description. They are not intended to be exhaustive of or to limit the invention to the precise forms disclosed. Many modifications and variations are possible in view of the above teachings. The embodiments are shown and described in order to best explain the principles of the invention and its practical applications, to thereby enable others skilled in the art to best utilize the invention and various embodiments with various modifications as are suited to the particular use contemplated.

Example 1

In order to test a sieving assembly incorporating a wiper blade therein, a sieving apparatus was fitted with a wiper blade that revolved at 50 rpm. The rotating coupon holder was fitted with four 1"×1" square glass coupons, and a mask having four 0.8"×0.8" square openings was applied over the coupon holder and coupons.

A sieve with 20 micron openings and containing a pre-fractionated load of from 0 to 38 microns was used, and sieving was carried out for 3 minutes to a coupon load of 30 micrograms/cm$^2$. Wiper blade sieving results in 10-20 times greater particle throughput as compared to sieves not incorporating a blade that contacts the sieving membrane, and prevents or reduces particle pooling. Use of the rotating coupon platform further evens out particle distribution. The vibration isolation provided by the rubber feet between the base of the rotating coupon platform and the collection pan limits particle redistribution after deposition on the coupons.

No vibratory or impact hammer assistance was used, and adequate particle uniformity across the multiple coupons was achieved by this system. An example of particle deposition on a coupon by sieving is found in FIG. 17B.

Example 2

In one implementation of the mechanical decoupling technique, custom cylindrical-shaped rubber feet were fabricated. The feet were designed to friction fit into 4 matching notches machined in the bottom side of the coupon holder and to protrude to lift the coupon holder away from the floor of the collection pan and enable the coupon holder to oscillate horizontally (shear mode). The friction fit design allows for easy cleaning and replacement for applications operating in a different frequency domain. It was found that the four feet provide suitable stability for the coupon holder while the vibration sieving operation was carried out.

The polymers considered for fabricating the feet were based on products from Smooth-On, Inc., of Macungie, Pa. In this comparative analysis, the Smooth-On, Inc. products Ecoflex® 00-30 and Dragon Skin® 20 were compared. Ecoflex® 00-30 has a Shore hardness of 30 based on the Shore 00 scale. This hardness is comparable to the hardness of the fleshy part of a normal healthy human fingertip. Dragon Skin® 20 is firmer and has a Shore hardness of 20 on the Shore A scale. The cylindrical feet were cast in custom-made molds and were fabricated with the dimensions of 24/64 inch height and ½ inch diameter.

After placing the completely assembled coupon holder with four Ecoflex® 00-30 rubber feet on the sieve collection pan, we observed the following during sieving procedures:
  Removal or absorption of any large amplitudes in the coupon holder originating from the vibrating sieve stack.
  Weakening of any vibration amplitude to a lower level.
  No increase above the natural frequency at different set vibration frequency levels.
These observations were made subjectively by contacting the coupon holder with a finger.

The feet fabricated using Dragon Skin® 20 were found to be too firm. The hard amplitude from the vibrating sieve stack was substantially transmitted through to the coupon holder and there was almost no weakening or absorption observed in the coupon vibration characteristics using the finger test.

Initial sieving tests conducted using the Ecoflex® 00-30 feet resulted in improved particle distribution (uniformity) across the entire coupon holder surface.

Example 3

The dust storm deposition technique is illustrated in FIG. 14. The system consists of a cylindrical container, an electrical fan (with power supply and controller), an appropriate substrate holder and the particles to be deposited on the substrate or coupon(s). The fan establishes a cyclonic airflow within the container which drives micron sized particles in a circular motion, and then lifts them up towards the top of the container where the particles adhere to one or more coupons.

The glass jar selected in the preliminary experiment described here was selected for convenience and to allow easy visual observations. The fan selected was a simple vane axial fan. The direction of the air flow was directed downwards towards the bottom of the glass jar. The rotational direction of the fan can be ignored. The two wires for power supply plus an additional wire without functionality held the fan in position. The lid of the jar contains a simple substrate holder which allows easy mounting and dismounting of a test coupon.

The first dust storm experiment did not incorporate the ball mill process and simply used material ground up with pestle and mortar and transferred into the glass jar. This test did not employ particles of certain fractionated size but still contained the target size between 1 and 30 microns (for fingerprint type particles). It also did not prevent particles from agglomerating together. But it was assumed there were enough small single particles which would adhere as desired to the coupon substrate. To break up possible agglomerations polyethylene (PE) beads were included with the particles. The PE beads where lightweight enough to flow with the particles and additionally allowed the air flow patterns to be more observable.

After turning on the fan, for approximately 10 seconds in total, a cyclonic airflow was observed through the movement of the PE beads. A close-up was filmed at 240 fps which afterwards confirmed that the particles followed the same cyclonic motion. The particles and beads were initially observed to rotate on the bottom of the jar, and after the cyclone was more established the particles and beads were lifted upwards while still rotating around the long axis of the container.

The coupon substrate was photomicrographed after the experiment. Analyses using Particle Math (developed by the U.S. Naval Research Laboratory, Washington, D.C.) established that the coverage achieved was about 2.5 µg/cm$^2$ and the effective diameters for the deposited particles were in the range of 1.4 to 25.8 µm. Particle distribution over the entire glass coupon was observed, shown in FIG. 17A. In addition, high particle adhesion was observed on all of the glass jar surfaces.

This initial dust storm experiment was deemed successful because it deposited the particle sizes of interest quickly and in a uniform fashion across the entire coupon. It may be possible that the dust storm apparatus operated in this experiment helped to filter or prevent larger particles from adhering to the coupon.

Example 4

A canister used in ball milling may be expanded with an interchangeable lid, to which is attached the fan blower and coupon holder from the preliminary dust storm study with a glass jar.

The fan was secured by 3 metal rods and a ring holder, which allowed the fan to be placed in different positions, as shown in FIG. 15. The coupon rested on a gasket on the outside of the lid and the can. This improvement allowed for a simple, quick exchange of coupons. The opening in the lid, which enables the particle deposition onto the coupon, is not limited in size or shape. The gasket prevents the substrate from resting directly on the lid surface and additionally prevents particles from escaping the can while the fan blower is being operated.

The same can used to mill particles is employed for dust storm generation by swapping out the lid for one with the fan blower and coupon assembly after ball milling. The freshly ground up material together with the ball bearings remain together inside the can during the dust storm. After the lid had been exchanged, the particle deposition via the dust storm was initiated. Depending on the amount of harvested, ground particles within the can, multiple coupons can be coated with particles.

This setup can be easily equipped with a dry air support, but that was not included in this example.

All parts within the can are covered with the ground up particles after the dust storm deposition.

A good distribution of particles across the coupon was observed, but there was also one problem identified. In one certain area the loading was much higher than in the rest. This was likely due to the thickness of the gasket used to secure the coupon, which allowed an airflow shadow. The coupons should be mounted as flush to the lid as possible to avoid additional turbulence that impacts the particle distribution on the coupon.

Example 5

In order to test a laser deposition apparatus, a blank substrate was placed beneath an upside-down glass coupon that included a high loading of particles (50-100 micrograms/$cm^2$). As a first step, an image of the glass coupon was taken and processed in situ, and the position and size of all particles on the coupon were catalogued. This image forms the particle stock from which particles can be printed on the blank glass substrate.

Desired particles were selected using the image of the glass coupon. Particles may be selected based on size, shape, or other considerations.

XY coordinates on the blank substrate where each particle should be deposited were then selected. For each selected particle, the first stage holding the loaded glass coupon was moved so that the particle is in the center of the image, where the laser is focused. Then, the second stage holding the blank substrate is moved to position the location on the blank where the particle is to be deposited directly beneath the particle on the first stage.

A $CO_2$ laser pulse was aimed at the location on the loaded coupon where the particle of interest was located, and fired to generate a miniature shock wave that travels to the other side of the glass coupon, knocking the particle of interest off of the loaded coupon. The particle free-falls onto the blank target substrate. Particle transfer was observed on the receiving substrate after the laser shock deposition process.

The $CO_2$ laser is absorbed by the top surface of the glass coupon, so no laser damage occurs to the particles or the glass optics used to guide the system. The distance between the loaded glass coupon and the target substrate is kept small so that no significant XY deviation occurs during freefall.

If particles of a certain type become exhausted in the image of the glass coupon, it is possible to move to a different part of the glass coupon, or load a new stock coupon into the device and repeat the image analysis, and continue printing on the same target coupon.

It will, of course, be appreciated that the above description has been given by way of example only and that modifications in detail may be made within the scope of the present invention.

Throughout this application, various patents and publications have been cited. The disclosures of these patents and publications in their entireties are hereby incorporated by reference into this application, in order to more fully describe the state of the art to which this invention pertains.

The invention is capable of modification, alteration, and equivalents in form and function, as will occur to those ordinarily skilled in the pertinent arts having the benefit of this disclosure. While the present invention has been described with respect to what are presently considered the preferred embodiments, the invention is not so limited. To the contrary, the invention is intended to cover various modifications and equivalent arrangements included within the spirit and scope of the description provided above.

What is claimed:

1. A particle printing apparatus comprising:

a first movable stage adapted to hold a first substrate having upper and lower surfaces, where particles are deposited on the lower surface;

an imaging system adapted to record a map comprising locations of particles deposited on the lower surface of the first substrate;

a second movable stage adapted to hold a second substrate designated for receiving particles deposited on the lower surface of the first substrate;

a laser; and a processor configured to select using the map recorded by the imaging system a particle of interest deposited on the lower surface of the first substrate, move the first movable stage to align the particle of interest with a beam from the laser, move the second movable stage to align the particle of interest with a location on said second substrate where the particle of interest is to be deposited, and energize the laser to produce a beam incident to the upper surface of the first substrate opposite to the particle of interest deposited on the lower surface, causing the particle of interest to be dislodged from the lower surface of the first substrate and fall onto the location on the second substrate.

2. The particle printing apparatus of claim 1, wherein a mask is incorporated between said first substrate and said second substrate to ensure only the intended particle has line of site to the second substrate and other particles which may become dislodged from the first substrate are captured by the mask and do not proceed to the second substrate.

3. The particle printing apparatus of claim 1, wherein the imaging system comprises a microscope and a camera.

4. The particle printing apparatus of claim 1, wherein the map comprises a photomicrograph.

5. The particle printing apparatus of claim 1, wherein the laser is a $CO_2$ laser.

* * * * *